(12) United States Patent
Cain et al.

(10) Patent No.: US 11,819,712 B2
(45) Date of Patent: *Nov. 21, 2023

(54) HISTOTRIPSY USING VERY SHORT ULTRASOUND PULSES

(71) Applicant: THE REGENTS OF THE UNIVERSITY OF MICHIGAN, Ann Arbor, MI (US)

(72) Inventors: Charles A. Cain, Ann Arbor, MI (US); Adam Maxwell, Seattle, WA (US); Zhen Xu, Ann Arbor, MI (US); Kuang-Wei Lin, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 434 days.

This patent is subject to a terminal disclaimer.

(21) Appl. No.: 17/008,369

(22) Filed: Aug. 31, 2020

(65) Prior Publication Data

US 2021/0008394 A1 Jan. 14, 2021

Related U.S. Application Data

(63) Continuation of application No. 14/911,273, filed as application No. PCT/US2014/052310 on Aug. 22, 2014, now Pat. No. 10,780,298.

(Continued)

(51) Int. Cl.
*A61N 7/00* (2006.01)
*A61B 17/32* (2006.01)

(52) U.S. Cl.
CPC .... *A61N 7/00* (2013.01); *A61B 2017/320069* (2017.08); *A61N 2007/003* (2013.01);

(Continued)

(58) Field of Classification Search
None
See application file for complete search history.

(56) References Cited

U.S. PATENT DOCUMENTS

| 3,243,497 A | 3/1966 | Kendall et al. |
| 3,679,021 A | 7/1972 | Goldberg et al. |

(Continued)

FOREIGN PATENT DOCUMENTS

| CA | 2910561 C | 7/2021 |
| CA | 2908740 C | 10/2021 |

(Continued)

OTHER PUBLICATIONS

Maxwell et al.; The role of compressional pressure in the formation of dense bubble clouds in histotripsy; 2009 IEEE International Ultrasonics Symposium; pp. 81-84; Sep. 20, 2009.

(Continued)

*Primary Examiner* — Amelie R Davis
(74) *Attorney, Agent, or Firm* — Shay Glenn LLP

(57) ABSTRACT

Apparatus and methods are provided for applying ultrasound pulses into tissue or a medium in which the peak negative pressure (P−) of one or more negative half cycle(s) of the ultrasound pulses exceed(s) an intrinsic threshold of the tissue or medium, to directly form a dense bubble cloud in the tissue or medium without shock-scattering. In one embodiment, a microtripsy method of Histotripsy therapy comprises delivering an ultrasound pulse from an ultrasound therapy transducer into tissue, the ultrasound pulse having at least a portion of a peak negative pressure half-cycle that exceeds an intrinsic threshold in the tissue to produce a bubble cloud of at least one bubble in the tissue, and generating a lesion in the tissue with the bubble cloud. The intrinsic threshold can vary depending on the type of tissue (Continued)

to be treated. In some embodiments, the intrinsic threshold in tissue can range from 15-30 MPa.

25 Claims, 5 Drawing Sheets

Related U.S. Application Data

(60) Provisional application No. 61/868,992, filed on Aug. 22, 2013.

(52) U.S. Cl.
CPC ............... *A61N 2007/0039* (2013.01); *A61N 2007/0065* (2013.01)

(56) References Cited

U.S. PATENT DOCUMENTS

| | | |
|---|---|---|
| 3,879,699 A | 4/1975 | Pepper |
| 4,016,749 A | 4/1977 | Wachter |
| 4,024,501 A | 5/1977 | Herring et al. |
| 4,051,394 A | 9/1977 | Tieden |
| 4,117,446 A | 9/1978 | Alais |
| 4,266,747 A | 5/1981 | Souder, Jr. et al. |
| 4,269,174 A | 5/1981 | Adair |
| 4,277,367 A | 7/1981 | Madsen et al. |
| 4,351,038 A | 9/1982 | Alais |
| 4,406,153 A | 9/1983 | Ophir et al. |
| 4,440,025 A | 4/1984 | Hayakawa et al. |
| 4,447,031 A | 5/1984 | Souder, Jr. et al. |
| 4,453,408 A | 6/1984 | Clayman |
| 4,483,343 A | 11/1984 | Beyer et al. |
| 4,483,345 A | 11/1984 | Miwa |
| 4,548,374 A | 10/1985 | Thompson et al. |
| 4,549,533 A | 10/1985 | Cain et al. |
| 4,550,606 A | 11/1985 | Drost |
| 4,551,794 A | 11/1985 | Sandell |
| 4,575,330 A | 3/1986 | Hull |
| 4,622,972 A | 11/1986 | Giebeler, Jr. |
| 4,625,731 A | 12/1986 | Quedens et al. |
| 4,641,378 A | 2/1987 | McConnell et al. |
| 4,669,483 A | 6/1987 | Hepp et al. |
| 4,689,986 A | 9/1987 | Carson et al. |
| 4,757,820 A | 7/1988 | Itoh |
| 4,791,915 A | 12/1988 | Barsotti et al. |
| 4,819,621 A | 4/1989 | Ueberle et al. |
| 4,829,491 A | 5/1989 | Saugeon et al. |
| 4,856,107 A | 8/1989 | Dory |
| 4,865,042 A | 9/1989 | Umemura et al. |
| 4,888,746 A | 12/1989 | Wurster et al. |
| 4,890,267 A | 12/1989 | Rudolph |
| 4,922,917 A | 5/1990 | Dory |
| 4,938,217 A | 7/1990 | Lele |
| 4,957,099 A | 9/1990 | Hassler |
| 4,973,980 A | 11/1990 | Howkins et al. |
| 4,984,575 A | 1/1991 | Uchiyama et al. |
| 4,991,151 A | 2/1991 | Dory |
| 4,995,012 A | 2/1991 | Dory |
| RE33,590 E | 5/1991 | Dory |
| 5,014,686 A | 5/1991 | Schafer |
| 5,065,751 A | 11/1991 | Wolf |
| 5,078,140 A | 1/1992 | Kwoh |
| 5,080,101 A | 1/1992 | Dory |
| 5,080,102 A | 1/1992 | Dory |
| 5,091,893 A | 2/1992 | Smith et al. |
| 5,092,336 A | 3/1992 | Fink |
| 5,097,709 A | 3/1992 | Masuzawa et al. |
| 5,111,822 A | 5/1992 | Dory |
| 5,143,073 A | 9/1992 | Dory |
| 5,143,074 A | 9/1992 | Dory |
| 5,150,711 A | 9/1992 | Dory |
| 5,158,070 A | 10/1992 | Dory |
| 5,158,071 A | 10/1992 | Umemura et al. |
| 5,163,421 A | 11/1992 | Bernstein et al. |
| 5,165,412 A | 11/1992 | Okazaki |
| 5,174,294 A | 12/1992 | Saito et al. |
| 5,209,221 A | 5/1993 | Riedlinger |
| 5,215,680 A | 6/1993 | D'Arrigo |
| 5,219,401 A | 6/1993 | Cathignol et al. |
| 5,222,806 A | 6/1993 | Roberts |
| 5,230,340 A | 7/1993 | Rhyne |
| 5,295,484 A | 3/1994 | Marcus et al. |
| 5,316,000 A | 5/1994 | Chapelon et al. |
| 5,354,258 A | 10/1994 | Dory |
| 5,380,411 A | 1/1995 | Schlief |
| 5,393,296 A | 2/1995 | Rattner |
| 5,409,002 A | 4/1995 | Pell |
| 5,431,621 A | 7/1995 | Dory |
| 5,435,311 A | 7/1995 | Umemura et al. |
| 5,443,069 A | 8/1995 | Schaetzle |
| 5,450,305 A | 9/1995 | Boys et al. |
| 5,469,852 A | 11/1995 | Nakamura et al. |
| 5,474,071 A | 12/1995 | Chapelon et al. |
| 5,474,531 A | 12/1995 | Carter |
| 5,490,051 A | 2/1996 | Messana |
| 5,492,126 A | 2/1996 | Hennige et al. |
| 5,501,655 A | 3/1996 | Rolt et al. |
| 5,520,188 A | 5/1996 | Hennige et al. |
| 5,523,058 A | 6/1996 | Umemura et al. |
| 5,524,620 A | 6/1996 | Rosenschein |
| 5,540,909 A | 7/1996 | Schutt |
| 5,542,935 A | 8/1996 | Unger et al. |
| 5,558,092 A | 9/1996 | Unger et al. |
| 5,563,346 A | 10/1996 | Bartelt et al. |
| 5,566,675 A | 10/1996 | Li et al. |
| 5,573,497 A | 11/1996 | Chapelon |
| 5,580,575 A | 12/1996 | Unger et al. |
| 5,582,578 A | 12/1996 | Zhong et al. |
| 5,590,657 A | 1/1997 | Cain et al. |
| 5,601,526 A | 2/1997 | Chapelon et al. |
| 5,617,862 A | 4/1997 | Cole et al. |
| 5,648,098 A | 7/1997 | Porter |
| 5,666,954 A | 9/1997 | Chapelon et al. |
| 5,676,452 A | 10/1997 | Scholz |
| 5,676,692 A | 10/1997 | Sanghvi et al. |
| 5,678,554 A | 10/1997 | Hossack et al. |
| 5,694,936 A | 12/1997 | Fujimoto et al. |
| 5,695,460 A | 12/1997 | Siegel et al. |
| 5,717,657 A | 2/1998 | Ruffa |
| 5,720,287 A | 2/1998 | Chapelon et al. |
| 5,724,972 A | 3/1998 | Petrofsky |
| 5,743,863 A | 4/1998 | Chapelon |
| 5,753,929 A | 5/1998 | Bliss |
| 5,759,162 A | 6/1998 | Oppelt et al. |
| 5,766,138 A | 6/1998 | Rattner |
| 5,769,790 A | 6/1998 | Watkins et al. |
| 5,797,848 A | 8/1998 | Marian et al. |
| 5,820,623 A | 10/1998 | Ng |
| 5,823,962 A | 10/1998 | Schaetzle et al. |
| 5,827,204 A | 10/1998 | Grandia et al. |
| 5,836,896 A | 11/1998 | Rosenschein |
| 5,849,727 A | 12/1998 | Porter et al. |
| 5,873,902 A | 2/1999 | Sanghvi et al. |
| 5,879,314 A | 3/1999 | Peterson et al. |
| 5,928,169 A | 7/1999 | Schitzle et al. |
| 5,932,807 A | 8/1999 | Mallart |
| 5,947,904 A | 9/1999 | Hossack et al. |
| 6,001,069 A | 12/1999 | Tachibana et al. |
| 6,022,309 A | 2/2000 | Celliers et al. |
| 6,036,667 A | 3/2000 | Manna et al. |
| 6,088,613 A | 7/2000 | Unger |
| 6,093,883 A | 7/2000 | Sanghvi et al. |
| 6,113,558 A | 9/2000 | Rosenschein et al. |
| 6,126,607 A | 10/2000 | Whitmore, III et al. |
| 6,128,958 A | 10/2000 | Cain |
| 6,143,018 A | 11/2000 | Beuthan et al. |
| 6,165,144 A | 12/2000 | Talish et al. |
| 6,176,842 B1 | 1/2001 | Tachibana et al. |
| 6,296,619 B1 | 10/2001 | Brisken et al. |
| 6,308,585 B1 | 10/2001 | Nilsson et al. |
| 6,308,710 B1 | 10/2001 | Silva |
| 6,309,355 B1 | 10/2001 | Cain et al. |
| 6,318,146 B1 | 11/2001 | Madsen et al. |

(56) References Cited

U.S. PATENT DOCUMENTS

| | | |
|---|---|---|
| 6,321,109 B2 | 11/2001 | Ben-Haim et al. |
| 6,338,566 B1 | 1/2002 | Verdier |
| 6,344,489 B1 | 2/2002 | Spears |
| 6,391,020 B1 | 5/2002 | Kurtz et al. |
| 6,413,216 B1 | 7/2002 | Cain et al. |
| 6,419,648 B1 | 7/2002 | Vitek et al. |
| 6,470,204 B1 | 10/2002 | Uzgiris et al. |
| 6,488,639 B1 | 12/2002 | Ribault et al. |
| 6,490,469 B2 | 12/2002 | Candy |
| 6,500,141 B1 | 12/2002 | Irion et al. |
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,428 B1 | 1/2003 | Azuma et al. |
| 6,511,444 B2 | 1/2003 | Hynynen et al. |
| 6,522,142 B1 | 2/2003 | Freundlich |
| 6,524,251 B2 | 2/2003 | Rabiner et al. |
| 6,536,553 B1 | 3/2003 | Scanlon |
| 6,543,272 B1 | 4/2003 | Vitek |
| 6,556,750 B2 | 4/2003 | Constantino et al. |
| 6,559,644 B2 | 5/2003 | Froundlich et al. |
| 6,576,220 B2 | 6/2003 | Unger |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugham, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,750,463 B1 | 6/2004 | Riley |
| 6,770,031 B2 | 8/2004 | Hynynen et al. |
| 6,775,438 B1 | 8/2004 | Gaedke et al. |
| 6,788,977 B2 | 9/2004 | Fenn et al. |
| 6,790,180 B2 | 9/2004 | Vitek |
| 6,820,160 B1 | 11/2004 | Allman |
| 6,852,082 B2 | 2/2005 | Strickberger et al. |
| 6,869,439 B2 | 3/2005 | White et al. |
| 6,890,332 B2 | 5/2005 | Truckai et al. |
| 6,929,609 B2 | 8/2005 | Asafusa |
| 7,004,282 B2 | 2/2006 | Manna et al. |
| 7,059,168 B2 | 6/2006 | Hibi et al. |
| 7,128,711 B2 | 10/2006 | Medan et al. |
| 7,128,719 B2 | 10/2006 | Rosenberg |
| 7,175,596 B2 | 2/2007 | Vitek et al. |
| 7,175,599 B2 | 2/2007 | Hynynen et al. |
| 7,196,313 B2 | 3/2007 | Quinones |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,359,640 B2 | 4/2008 | Onde et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,429,249 B1 | 9/2008 | Winder et al. |
| 7,431,704 B2 | 10/2008 | Babaev |
| 7,442,168 B2 | 10/2008 | Novak et al. |
| 7,462,488 B2 | 12/2008 | Madsen et al. |
| 7,559,905 B2 | 7/2009 | Kagosaki et al. |
| 7,656,638 B2 | 2/2010 | Laakso et al. |
| 7,695,437 B2 | 4/2010 | Quistgaard et al. |
| 7,714,481 B2 | 5/2010 | Sakai |
| 7,771,359 B2 | 8/2010 | Adam |
| 7,967,763 B2 | 6/2011 | Deem et al. |
| 8,057,408 B2 | 11/2011 | Cain et al. |
| 8,295,912 B2 | 10/2012 | Gertner |
| 8,333,115 B1 | 12/2012 | Garvey et al. |
| 8,337,407 B2 | 12/2012 | Quistgaard et al. |
| 8,342,467 B2 | 1/2013 | Stachowski et al. |
| 8,376,970 B2 | 2/2013 | Babaev |
| 8,539,813 B2 | 9/2013 | Cain et al. |
| 8,568,339 B2 | 10/2013 | Rybyanets |
| 8,636,664 B2 | 1/2014 | Brannan |
| 8,715,187 B2 | 5/2014 | Landberg Davis et al. |
| 8,845,537 B2 | 9/2014 | Tanaka et al. |
| 8,932,239 B2 | 1/2015 | Sokka et al. |
| 9,028,434 B2 | 5/2015 | Tanaka |
| 9,049,783 B2 | 6/2015 | Teofilovic |
| 9,061,131 B2 | 6/2015 | Jahnke et al. |
| 9,144,694 B2 | 9/2015 | Cain |
| 9,220,476 B2 | 12/2015 | Coussios et al. |
| 9,228,730 B1 | 1/2016 | Inbody |
| 9,302,124 B2 | 4/2016 | Konofagou et al. |
| 9,457,201 B2 | 10/2016 | Hoelscher et al. |
| 9,526,923 B2 | 12/2016 | Jahnke et al. |
| 9,636,133 B2 | 5/2017 | Hall et al. |
| 9,642,634 B2 | 5/2017 | Cain et al. |
| 9,763,688 B2 | 9/2017 | Stulen et al. |
| 9,901,753 B2 | 2/2018 | Cain et al. |
| 9,943,708 B2 | 4/2018 | Roberts et al. |
| 10,046,181 B2 | 8/2018 | Barthe et al. |
| 10,058,352 B2 | 8/2018 | Carvell et al. |
| 10,071,266 B2 | 9/2018 | Cain |
| 10,130,828 B2 | 11/2018 | Vortman et al. |
| 10,219,815 B2 | 3/2019 | Maxwell et al. |
| 10,293,187 B2 | 5/2019 | Cannata et al. |
| 10,751,125 B2 | 8/2020 | Levy et al. |
| 10,780,298 B2 | 9/2020 | Cain et al. |
| 10,791,991 B2 | 10/2020 | Burkett et al. |
| 10,799,209 B2 | 10/2020 | Lahti et al. |
| 10,820,813 B2 | 11/2020 | Alpert |
| 10,847,264 B2 | 11/2020 | Mansker et al. |
| 10,849,511 B2 | 12/2020 | Tochterman et al. |
| 10,869,603 B2 | 12/2020 | Millett et al. |
| 10,869,633 B2 | 12/2020 | Burkett |
| 10,869,648 B2 | 12/2020 | Hubbard et al. |
| 10,874,353 B2 | 12/2020 | Assif |
| 10,874,409 B2 | 12/2020 | Matsubara et al. |
| 10,888,232 B2 | 1/2021 | Anderson et al. |
| 10,893,808 B2 | 1/2021 | Dorando |
| 10,912,463 B2 | 2/2021 | Davies et al. |
| 10,925,688 B2 | 2/2021 | Millett et al. |
| 10,927,003 B2 | 2/2021 | Millett et al. |
| 10,932,678 B2 | 3/2021 | Burkett |
| 10,939,826 B2 | 3/2021 | Glynn et al. |
| 10,942,022 B2 | 3/2021 | Johansson et al. |
| 10,973,419 B2 | 4/2021 | Corl |
| 10,993,618 B2 | 5/2021 | Mansker et al. |
| 10,993,628 B2 | 5/2021 | Tochterman |
| 10,993,694 B2 | 5/2021 | Meyer et al. |
| 11,000,185 B2 | 5/2021 | Stigall et al. |
| 11,006,840 B2 | 5/2021 | Stigall |
| 11,013,491 B2 | 5/2021 | Rice et al. |
| 11,020,087 B2 | 6/2021 | Hoffman |
| 11,026,591 B2 | 6/2021 | Burkett et al. |
| 11,040,140 B2 | 6/2021 | Unser et al. |
| 11,112,473 B2 | 9/2021 | Assif |
| 11,119,552 B2 | 9/2021 | Spencer et al. |
| 11,120,896 B2 | 9/2021 | Balignasay et al. |
| 11,141,063 B2 | 10/2021 | Kemp et al. |
| 11,141,131 B2 | 10/2021 | Stigall et al. |
| 11,219,748 B2 | 1/2022 | Burkett et al. |
| 11,224,349 B2 | 1/2022 | Davies et al. |
| 11,224,403 B2 | 1/2022 | Cori |
| 11,234,649 B2 | 2/2022 | Matsubara et al. |
| 11,246,533 B2 | 2/2022 | Henderson et al. |
| 11,253,225 B2 | 2/2022 | Hancock et al. |
| 11,260,160 B2 | 3/2022 | Matsubara et al. |

(56) References Cited

U.S. PATENT DOCUMENTS

| | | |
|---|---|---|
| 11,272,845 B2 | 3/2022 | Cheline et al. |
| 11,298,030 B2 | 4/2022 | Davies et al. |
| 11,311,271 B2 | 4/2022 | Stigall et al. |
| 11,324,410 B2 | 5/2022 | Burkett |
| 11,369,346 B2 | 6/2022 | De Cicco et al. |
| 11,369,994 B2 | 6/2022 | Greenberg et al. |
| 11,406,498 B2 | 8/2022 | Stigall et al. |
| 11,413,017 B2 | 8/2022 | Stigall et al. |
| 11,471,215 B2 | 10/2022 | Stigall et al. |
| 2001/0039420 A1 | 11/2001 | Burbank et al. |
| 2001/0041163 A1 | 11/2001 | Sugita et al. |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2002/0145091 A1 | 10/2002 | Talish et al. |
| 2003/0092982 A1 | 5/2003 | Eppstein |
| 2003/0112922 A1 | 6/2003 | Burdette et al. |
| 2003/0149352 A1 | 8/2003 | Liang et al. |
| 2003/0157025 A1 | 8/2003 | Unger et al. |
| 2003/0169591 A1 | 9/2003 | Cochran |
| 2003/0181833 A1 | 9/2003 | Faragalla et al. |
| 2003/0199857 A1 | 10/2003 | Eizenhofer |
| 2003/0221561 A1 | 12/2003 | Milo |
| 2003/0236539 A1 | 12/2003 | Rabiner et al. |
| 2004/0127815 A1 | 7/2004 | Marchitto et al. |
| 2004/0138563 A1 | 7/2004 | Moehring et al. |
| 2004/0162571 A1 | 8/2004 | Rabiner et al. |
| 2004/0236248 A1 | 11/2004 | Svedman |
| 2004/0243021 A1 | 12/2004 | Murphy et al. |
| 2004/0260214 A1 | 12/2004 | Echt et al. |
| 2005/0020945 A1 | 1/2005 | Tosaya et al. |
| 2005/0038339 A1 | 2/2005 | Chauhan et al. |
| 2005/0038361 A1 | 2/2005 | Zhong et al. |
| 2005/0152561 A1 | 7/2005 | Spencer |
| 2005/0154314 A1 | 7/2005 | Quistgaard |
| 2005/0154431 A1 | 7/2005 | Quistgaard et al. |
| 2005/0203399 A1* | 9/2005 | Vaezy .................. A61B 8/0833 600/439 |
| 2005/0215901 A1 | 9/2005 | Anderson et al. |
| 2005/0234438 A1 | 10/2005 | Mast et al. |
| 2005/0283098 A1 | 12/2005 | Conston et al. |
| 2006/0060991 A1 | 3/2006 | Holsteyns et al. |
| 2006/0074303 A1 | 4/2006 | Chomenky et al. |
| 2006/0089636 A1 | 4/2006 | Christopherson et al. |
| 2006/0173321 A1 | 8/2006 | Kubota et al. |
| 2006/0173387 A1 | 8/2006 | Hansmann et al. |
| 2006/0206028 A1 | 9/2006 | Lee et al. |
| 2006/0241466 A1 | 10/2006 | Ottoboni et al. |
| 2006/0241523 A1 | 10/2006 | Sinelnikov et al. |
| 2006/0241533 A1 | 10/2006 | Geller |
| 2006/0264760 A1 | 11/2006 | Liu et al. |
| 2006/0293598 A1 | 12/2006 | Fraser |
| 2006/0293630 A1 | 12/2006 | Manna et al. |
| 2007/0010805 A1 | 1/2007 | Fedewa et al. |
| 2007/0016039 A1 | 1/2007 | Vortman et al. |
| 2007/0044562 A1 | 3/2007 | Sam |
| 2007/0065420 A1 | 3/2007 | Johnson |
| 2007/0083120 A1 | 4/2007 | Cain et al. |
| 2007/0161902 A1 | 7/2007 | Dan |
| 2007/0167764 A1 | 7/2007 | Hynynen |
| 2007/0205785 A1 | 9/2007 | Nilsson |
| 2007/0219448 A1 | 9/2007 | Seip et al. |
| 2007/0239001 A1 | 10/2007 | Mehl et al. |
| 2008/0013593 A1 | 1/2008 | Kawabata |
| 2008/0033297 A1 | 2/2008 | Sliwa |
| 2008/0033417 A1 | 2/2008 | Nields et al. |
| 2008/0051656 A1 | 2/2008 | Vaezy et al. |
| 2008/0055003 A1 | 3/2008 | Unnikrishnan et al. |
| 2008/0082026 A1 | 4/2008 | Schmidt et al. |
| 2008/0091125 A1 | 4/2008 | Owen et al. |
| 2008/0126665 A1 | 5/2008 | Burr et al. |
| 2008/0154132 A1 | 6/2008 | Hall et al. |
| 2008/0167555 A1 | 7/2008 | Qian et al. |
| 2008/0177180 A1 | 7/2008 | Azhari et al. |
| 2008/0194965 A1 | 8/2008 | Sliwa et al. |
| 2008/0214964 A1 | 9/2008 | Chapelon et al. |
| 2008/0262345 A1 | 10/2008 | Fichtinger et al. |
| 2008/0262486 A1 | 10/2008 | Zvuloni et al. |
| 2008/0312561 A1 | 12/2008 | Chauhan |
| 2008/0319356 A1* | 12/2008 | Cain .................. A61M 37/0092 600/300 |
| 2008/0319376 A1 | 12/2008 | Wilcox et al. |
| 2009/0030339 A1 | 1/2009 | Cheng et al. |
| 2009/0036773 A1 | 2/2009 | Lau et al. |
| 2009/0112098 A1 | 4/2009 | Vaezy et al. |
| 2009/0198094 A1 | 8/2009 | Fenster |
| 2009/0211587 A1 | 8/2009 | Lawrentschuk |
| 2009/0227874 A1 | 9/2009 | Suri et al. |
| 2009/0230822 A1 | 9/2009 | Kushculey et al. |
| 2009/0254008 A1 | 10/2009 | Shields, Jr. |
| 2009/0287083 A1 | 11/2009 | Kushculey et al. |
| 2010/0011845 A1 | 1/2010 | Laugharn et al. |
| 2010/0056924 A1 | 3/2010 | Powers |
| 2010/0059264 A1 | 3/2010 | Hasegawa et al. |
| 2010/0069797 A1 | 3/2010 | Cain et al. |
| 2010/0125225 A1 | 5/2010 | Gelbart et al. |
| 2010/0152624 A1 | 6/2010 | Tanis et al. |
| 2010/0163694 A1 | 7/2010 | Fadler et al. |
| 2010/0261994 A1 | 10/2010 | Davalos et al. |
| 2010/0274136 A1 | 10/2010 | Cerofolini |
| 2010/0286519 A1 | 11/2010 | Lee et al. |
| 2010/0298744 A1 | 11/2010 | Altshuler et al. |
| 2010/0305432 A1 | 12/2010 | Duhay et al. |
| 2010/0317971 A1 | 12/2010 | Fan et al. |
| 2010/0318002 A1 | 12/2010 | Prus et al. |
| 2011/0054315 A1* | 3/2011 | Roberts .................. A61B 8/4218 600/439 |
| 2011/0112400 A1 | 5/2011 | Emery et al. |
| 2011/0118602 A1 | 5/2011 | Weng et al. |
| 2011/0144490 A1 | 6/2011 | Davis et al. |
| 2011/0144545 A1 | 6/2011 | Fan et al. |
| 2011/0172529 A1 | 7/2011 | Gertner |
| 2011/0178444 A1 | 7/2011 | Slayton et al. |
| 2011/0245671 A1 | 10/2011 | Sato |
| 2011/0251528 A1 | 10/2011 | Canney et al. |
| 2011/0257524 A1 | 10/2011 | Gertner |
| 2011/0263967 A1 | 10/2011 | Bailey et al. |
| 2011/0270136 A1 | 11/2011 | Vitek et al. |
| 2011/0319927 A1 | 12/2011 | Nita |
| 2012/0029337 A1 | 2/2012 | Aoyagi |
| 2012/0029353 A1 | 2/2012 | Slayton et al. |
| 2012/0029393 A1 | 2/2012 | Lee |
| 2012/0059264 A1 | 3/2012 | Hope Simpson et al. |
| 2012/0059285 A1 | 3/2012 | Soltani et al. |
| 2012/0092724 A1 | 4/2012 | Pettis |
| 2012/0111339 A1 | 5/2012 | Barthe et al. |
| 2012/0130288 A1 | 5/2012 | Holland et al. |
| 2012/0136279 A1 | 5/2012 | Tanaka et al. |
| 2012/0158013 A1 | 6/2012 | Stefanchik et al. |
| 2012/0172720 A1 | 7/2012 | Asami et al. |
| 2012/0189998 A1 | 7/2012 | Kruecker et al. |
| 2012/0215157 A1 | 8/2012 | Berryman et al. |
| 2012/0232388 A1 | 9/2012 | Curra et al. |
| 2012/0259250 A1 | 10/2012 | Sapozhnikov et al. |
| 2012/0271167 A1 | 10/2012 | Holland et al. |
| 2012/0271223 A1 | 10/2012 | Khanna |
| 2013/0051178 A1 | 2/2013 | Rybyanets |
| 2013/0053691 A1 | 2/2013 | Kawabata et al. |
| 2013/0090579 A1 | 4/2013 | Cain et al. |
| 2013/0102932 A1 | 4/2013 | Cain et al. |
| 2013/0144165 A1 | 6/2013 | Ebbini et al. |
| 2013/0190623 A1 | 7/2013 | Bertolina et al. |
| 2013/0190661 A1 | 7/2013 | Wing et al. |
| 2013/0255426 A1 | 10/2013 | Kassow et al. |
| 2013/0303906 A1 | 11/2013 | Cain et al. |
| 2014/0030806 A1 | 1/2014 | Dudley et al. |
| 2014/0046181 A1 | 2/2014 | Benchimol et al. |
| 2014/0058293 A1 | 2/2014 | Hynynen et al. |
| 2014/0073995 A1 | 3/2014 | Teofilovic et al. |
| 2014/0074076 A1 | 3/2014 | Gertner |
| 2014/0088613 A1 | 3/2014 | Seo et al. |
| 2014/0100459 A1 | 4/2014 | Xu et al. |
| 2014/0112107 A1 | 4/2014 | Guo et al. |
| 2014/0128734 A1 | 5/2014 | Genstler et al. |

(56) References Cited

U.S. PATENT DOCUMENTS

| | | |
|---|---|---|
| 2014/0200489 A1 | 7/2014 | Behar et al. |
| 2014/0243664 A1 | 8/2014 | El-Sayed et al. |
| 2014/0330124 A1 | 11/2014 | Carol |
| 2014/0378832 A1 | 12/2014 | Sanghvi et al. |
| 2015/0063668 A1 | 3/2015 | You et al. |
| 2015/0073261 A1 | 3/2015 | Kohler et al. |
| 2015/0080926 A1* | 3/2015 | Emery ............... A61B 90/37 606/169 |
| 2015/0151141 A1 | 6/2015 | Arnal et al. |
| 2015/0190121 A1 | 7/2015 | Slayton et al. |
| 2015/0190659 A1 | 7/2015 | Kolher |
| 2015/0224347 A1 | 8/2015 | Barthe et al. |
| 2015/0258352 A1 | 9/2015 | Lin et al. |
| 2015/0273246 A1 | 10/2015 | Darlington et al. |
| 2015/0297177 A1 | 10/2015 | Boctor et al. |
| 2016/0004933 A1 | 1/2016 | Hu et al. |
| 2016/0135916 A1 | 5/2016 | Rakic et al. |
| 2016/0151618 A1 | 6/2016 | Powers et al. |
| 2016/0184614 A1 | 6/2016 | Matula et al. |
| 2016/0206867 A1 | 7/2016 | Hossack et al. |
| 2016/0249859 A1 | 9/2016 | Babkin et al. |
| 2016/0287909 A1 | 10/2016 | Maxwell et al. |
| 2016/0331585 A1 | 11/2016 | Kim |
| 2016/0339273 A1 | 11/2016 | Al Mayiah |
| 2016/0354087 A1 | 12/2016 | Noonan et al. |
| 2016/0361574 A1 | 12/2016 | Barthe et al. |
| 2017/0000376 A1 | 1/2017 | Partanen et al. |
| 2017/0049463 A1 | 2/2017 | Popovic et al. |
| 2017/0071515 A1 | 3/2017 | Chevillet et al. |
| 2017/0072227 A1 | 3/2017 | Khokhlova et al. |
| 2017/0072228 A1 | 3/2017 | Wang et al. |
| 2017/0165046 A1 | 6/2017 | Johnson et al. |
| 2017/0232277 A1 | 8/2017 | Hall et al. |
| 2018/0049719 A1 | 2/2018 | Xu et al. |
| 2018/0154186 A1 | 6/2018 | Xu et al. |
| 2018/0161086 A1 | 6/2018 | Davalos et al. |
| 2019/0023804 A1 | 1/2019 | Onik et al. |
| 2019/0216478 A1 | 7/2019 | Maxwell et al. |
| 2019/0275353 A1 | 9/2019 | Cannata et al. |
| 2019/0282294 A1 | 9/2019 | Davalos et al. |
| 2020/0010575 A1 | 1/2020 | Hode et al. |
| 2020/0164231 A1 | 5/2020 | Cannata et al. |
| 2020/0253550 A1 | 8/2020 | Nair |
| 2020/0260964 A1 | 8/2020 | Collins et al. |
| 2020/0330039 A1 | 10/2020 | Burkett et al. |
| 2020/0330075 A1 | 10/2020 | O'Reilly et al. |
| 2021/0000541 A1 | 1/2021 | Levy et al. |
| 2021/0022703 A1 | 1/2021 | Nair |
| 2021/0161398 A1 | 6/2021 | Millett et al. |
| 2021/0353161 A1 | 11/2021 | Merritt et al. |
| 2021/0401400 A1 | 12/2021 | Sheehan et al. |
| 2022/0079563 A1 | 3/2022 | Kemp |
| 2022/0257329 A1 | 8/2022 | Stigall et al. |
| 2022/0280233 A1 | 9/2022 | Park et al. |

FOREIGN PATENT DOCUMENTS

| | | |
|---|---|---|
| CA | 2840014 C | 8/2023 |
| CN | 1669672 A | 9/2005 |
| CN | 1732031 A | 2/2006 |
| CN | 201197744 Y | 2/2009 |
| CN | 102292123 A | 12/2011 |
| CN | 102481164 A | 5/2012 |
| CN | 102665585 A | 9/2012 |
| CN | 103537016 A | 1/2014 |
| CN | 103648361 A | 3/2014 |
| CN | 103812477 A | 5/2014 |
| CN | 104013444 A | 9/2014 |
| CN | 104135938 A | 11/2014 |
| CN | 106661535 B | 3/2021 |
| CN | 2908740 C | 10/2021 |
| CN | 113705586 A | 11/2021 |
| DE | 3220751 A1 | 12/1983 |
| DE | 3544628 A1 | 6/1987 |
| DE | 3817094 A1 | 11/1989 |
| DE | 4012760 A1 | 5/1992 |
| EP | 0017382 A1 | 10/1980 |
| EP | 0320303 A2 | 6/1989 |
| EP | 0332871 A2 | 9/1989 |
| EP | 0384831 A2 | 8/1990 |
| EP | 0755653 A1 | 1/1997 |
| EP | 1374785 A1 | 1/2004 |
| EP | 1504713 A1 | 2/2005 |
| EP | 2397188 A1 | 12/2011 |
| EP | 2934308 B1 | 10/2015 |
| EP | 2934309 B1 | 10/2015 |
| EP | 3097180 B1 | 11/2016 |
| EP | 2759003 B1 | 8/2020 |
| EP | 2887989 B1 | 2/2021 |
| EP | 3777689 A1 | 2/2021 |
| EP | 2938253 B1 | 3/2021 |
| EP | 3076864 B1 | 3/2021 |
| EP | 2802276 B1 | 4/2021 |
| EP | 2809221 B1 | 4/2021 |
| EP | 2967369 B1 | 5/2021 |
| EP | 2967488 B1 | 6/2021 |
| EP | 3184048 B1 | 6/2021 |
| EP | 2967370 B1 | 9/2021 |
| EP | 2931130 B1 | 10/2021 |
| EP | 2934304 B1 | 10/2021 |
| EP | 3888534 A1 | 10/2021 |
| EP | 3895604 A1 | 10/2021 |
| EP | 3903672 A1 | 11/2021 |
| EP | 2964096 B1 | 12/2021 |
| EP | 3545829 B1 | 3/2022 |
| EP | 3060129 B1 | 4/2022 |
| EP | 2914166 B1 | 5/2022 |
| EP | 2779907 B1 | 6/2022 |
| EP | 3102098 B1 | 6/2022 |
| EP | 2965263 B1 | 7/2022 |
| EP | 2726152 B1 | 8/2022 |
| EP | 4042936 A1 | 8/2022 |
| EP | 3298959 B2 | 9/2022 |
| EP | 2931131 B1 | 11/2022 |
| EP | 2938268 B1 | 11/2022 |
| EP | 3581103 B1 | 11/2022 |
| EP | 2950737 B1 | 1/2023 |
| EP | 2869804 B1 | 2/2023 |
| EP | 2938265 B1 | 2/2023 |
| EP | 3024403 B1 | 3/2023 |
| EP | 4151156 A1 | 3/2023 |
| EP | 2938271 B1 | 4/2023 |
| EP | 4179995 A2 | 5/2023 |
| EP | 2866733 B1 | 9/2023 |
| ES | 2819552 T3 | 4/2021 |
| GB | 2099582 A | 12/1982 |
| IN | 387413 B | 1/2022 |
| JP | 60-80779 A | 5/1985 |
| JP | 61-196718 A | 8/1986 |
| JP | 02-215451 A | 8/1990 |
| JP | H0422351 A | 1/1992 |
| JP | 06-197907 A | 7/1994 |
| JP | 07-504339 A | 5/1995 |
| JP | 08-84740 A | 4/1996 |
| JP | 06-304178 A | 5/1996 |
| JP | 08-131454 A | 5/1996 |
| JP | 09-55571 A | 2/1997 |
| JP | 10-512477 A | 12/1998 |
| JP | 2000300559 A | 10/2000 |
| JP | 2003510159 A | 3/2003 |
| JP | 2004505660 A | 2/2004 |
| JP | 2004249106 A | 9/2004 |
| JP | 2005167058 A | 6/2005 |
| JP | 2006511265 A | 4/2006 |
| JP | 2007144225 A | 6/2007 |
| JP | 2007520307 A | 7/2007 |
| JP | 2010019554 A | 1/2010 |
| JP | 2010029650 A | 2/2010 |
| JP | 2010204068 A | 9/2010 |
| JP | 2013538097 A | 10/2013 |
| JP | 2004512502 A | 4/2014 |
| JP | 2015519970 A | 7/2015 |
| JP | 2016508808 A | 3/2016 |

(56) References Cited

FOREIGN PATENT DOCUMENTS

| JP | 06785554 | B2 | 10/2020 |
|---|---|---|---|
| JP | 6979633 | B2 | 12/2021 |
| JP | 7171645 | B2 | 11/2022 |
| WO | WO94/06355 | A1 | 3/1994 |
| WO | WO02/32506 | A1 | 4/2002 |
| WO | WO2005/018469 | A1 | 3/2005 |
| WO | WO2008/051484 | A2 | 5/2008 |
| WO | WO2011/040054 | A1 | 7/2011 |
| WO | WO2011/092683 | A1 | 8/2011 |
| WO | WO2011/154654 | A2 | 12/2011 |
| WO | WO2014/008594 | A1 | 1/2014 |
| WO | WO2014/071386 | A1 | 5/2014 |
| WO | WO2015/000953 | A1 | 1/2015 |

OTHER PUBLICATIONS

Xu et al.; U.S. Appl. No. 17/161,498 entitled Systems and methods for histotripsy immunosensitization, filed Jan. 28, 2021.

Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.

Appel et al.; Stereoscopic highspeed recording of bubble filaments; Ultrasonics Sonochemistry; vol. 11(1); pp. 39-42; Jan. 2004.

Arani et al.; Transurethral prostate magnetic resonance elestography; prospective imaging requirements; Magn. Reson. Med.; 65(2); pp. 340-349; Feb. 2011.

Aschoff et al.; How does alteration of hepatic blood flow affect liver perfusion and radiofrequency-induced thermal lesion size in rabbit liver ?; J Magn Reson Imaging; 13(1); pp. 57-63; Jan. 2001.

Atchley et al.; Thresholds for cavitation produced in water by pulsed ultrasound; Ultrasonics.; vol. 26(5); pp. 280-285; Sep. 1988.

Avago Technologies; ACNV2601 High Insulation Voltage 10 MBd Digital Opotcoupler. Avago Technologies Data Sheet; pp. 1-11; Jul. 29, 2010.

Avago Technologies; Avago's ACNV2601 optocoupler is an optically coupled logic gate; Data Sheet; 2 pages; Jul. 29, 2010.

Avtech; AVR-8 Data sheet; May 23, 2004; 3 pages; retrieved from the internet (http//www.avtechpulse.com).

Bak; Rapid protytyping or rapid production? 3D printing processes move industry towards the latter; Assembly Automation; 23(4); pp. 340-345; Dec. 1, 2003.

Billson et al.; Rapid prototyping technologies for ultrasonic beam focussing in NDE; IEEE International Ultrasonic Symposium Proceedings; pp. 2472-2474; Oct. 2011.

Bjoerk et al.; Cool/MOS CP—How to make most beneficial use of the generation of super junction technology devices. Infineon Technologies AG. [retrieved Feb. 4, 2014] from the internet (http://www.infineon.com/dgdl/infineon+-+Application+Note+-+PowerMOSFETs+-+600V+CoolMOS%E284%A2+-+CP+Most+beneficial+use+of+superjunction+technologie+devices.pdf?folderid=db3a304412b407950112b408e8c90004&fileid=db3a304412b407950112b40ac9a40688>pp. 1, 4, 14; Feb. 2007.

Bland et al.; Surgical Oncology; McGraw Hill; Chap. 5 (Cavitron Ultrasonic Aspirator); pp. 461-462; Jan. 29, 2001.

Burdin et al.; Implementation of the laser diffraction technique for cavitation bubble investigations; Particle & Particle Systems Characterization; vol. 19; pp. 73-83; May 2002.

Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.

Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).

Chan et al.; An image-guided high intensity focused ultrasound device for uterine fibroids treatment; Medical Physics, vol. 29, pp. 2611-2620, Nov. 2002.

Clasen et al.; MR-guided radiofrequency ablation of hepatocellular carcinoma: Long-term effectiveness; J Vasc Interv Radiol; 22(6); pp. 762-770; Jun. 2011.

Clement et al.; A hemisphere array for non-invasive ultrasound brain therapy and surgery; Physics in Medicine and Biology, vol. 45, p. 3707-3719, Dec. 2000.

Cline et al.; Magnetic resonance-guided thermal surgery; Magnetic Resonance in Medicine; 30(1); pp. 98-106; Jul. 1993.

Curiel et al.; Elastography for the follow-up of high-intensity focused ultrasound prostate cancer treatment: Initial comparison with MRI; Ultrasound Med. Biol; 31(11); pp. 1461-1468; Nov. 2005.

Desilets et al.; The Design of Efficient Broad-Band Piezoelectric Transducers; Sonics and Ultrasonics, IEEE Transactions on, vol. 25, pp. 115-125, May 1978.

Emelianov et al.; Triplex ultrasound: Elasticity imaging to age deep venous thrombosis; Ultrasound Med Biol; 28(6); pp. 757-767; Jun. 2002.

Giannatsis et al.; Additive fabrication technologies applied to medicine and health care: a review; The International Journal of Advanced Manufacturing Technology; 40(1-2); pp. 116-127; Jan. 2009.

Gudra et al.; Influence of acoustic impedance of multilayer acoustic systems on the transfer function of ultrasonic airborne transducers; Ultrasonics, vol. 40, pp. 457-463, May 2002.

Hall et al.; A Low Cost Compact 512 Channel Therapeutic Ultrasound System for Transcutaneous Ultrasound Surgery; AIP Conference Proceedings, Boston, MA; vol. 829, pp. 445-449, Oct. 27-29, 2005.

Hall et al.; Acoustic Access to the Prostate for Extracorporeal Ultrasound Ablation; Journal of Endourology, vol. 24, pp. 1875-1881, Nov. 2010.

Hall et al.; Histotripsy of the prostate: dose effects in a chronic canine model; Urology; 74(4); pp. 932-937; Oct. 2009 (author manuscript).

Hall et al.; Imaging feedback of tissue liquefaction (histotripsy) in ultrasound surgery; IEEE Ultrasonic Symposium, Sep. 18-21, 2005, pp. 1732-1734.

Hartmann; Ultrasonic properties of poly(4-methyl pentene-1), Journal of Applied Physics, vol. 51, pp. 310-314, Jan. 1980.

Hobarth et al.; Color flow doppler sonography for extracorporal shock wave lithotripsy; Journal of Urology; 150(6); pp. 1768-1770; Dec. 1, 1993.

Holland et al.; Thresholds for transient cavitation produced by pulsed ultrasound in a controlled nuclei environment; J. Acoust. Soc. Am.; vol. 88(5); pp. 2059-2069; Nov. 1990.

Huber et al.; Influence of shock wave pressure amplitude and pulse repetition frequency on the lifespan, size and number of transient cavities in the field of an electromagnetic lithotripter; Physics in Medicine and Biology; vol. 43(10); pp. 3113-3128; Oct. 1998.

Hynynen et al.; Tissue thermometry during ultrasound exposure; European Urology; 23(Suppl 1); pp. 12-16; (year of pub. sufficiently earlier than effective US filing date and any foreign priority date)1993.

Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.

Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.

Kim et al.; Dependence of particle volume fraction on sound velocity and attenuation of EPDM composites; Ultrasonics, vol. 46, pp. 177-183, Feb. 2007.

Konofagou; Quo vadis elasticity imaging ?; Ultrasonics; 42(1-9); pp. 331-336; Apr. 2004.

Krimholtz et al.; New equivalent circuits for elementary piezoelectric transducers; Electronics Letters, vol. 6, pp. 398-399, Jun. 1970.

Kruse et al.; Tissue characterization using magnetic resonance elastography: Preliminary results; Phys. Med. Biol; 45(6); pp. 1579-1590; Jun. 2000.

(56) References Cited

OTHER PUBLICATIONS

Lake et al.; Histotripsy: minimally invasive technology for prostatic tissue ablation in an in vivo canine model; Urology; 72(3); pp. 682-686; Sep. 2008.

Lauterborn et al.; Cavitation bubble dynamics studied by high speed photography and holography: part one; Ultrasonics; vol. 23; pp. 260-268; Nov. 1985.

Lensing et al.; Deep-vein thrombosis; The Lancet, vol. 353, pp. 479-485, Feb. 6, 1999.

Lin et al.; Dual-beam histotripsy: a low-frequency pump enabling a high-frequency probe for precise lesion formation; IEEE Trans. Ultrason. Ferroelectr. Control; 61(2); pp. 325-340; Feb. 2014; (Author Manuscript; 29 pages).

Liu et al.; Real-time 2-D temperature imaging using ultrasound; IEEE Trans Biomed Eng; 57(1); pp. 12-16; Jan. 2010 (author manuscript, 16 pgs.).

Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).

Manes et al.; Design of a Simplified Delay System for Ultrasound Phased Array Imaging; Sonics and Ultrasonics, IEEE Transactions on, vol. 30, pp. 350-354, Nov. 1983.

Maréchal et al; Effect of Radial Displacement of Lens on Response of Focused Ultrasonic Transducer; Japanese Journal of Applied Physics, vol. 46, p. 3077-3085; May 15, 2007.

Maréchal et al; Lens-focused transducer modeling using an extended KLM model; Ultrasonics, vol. 46, pp. 155-167, May 2007.

Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.

Maxwell et al.; Cavitation clouds created by shock scattering from bubbles during histotripsy; J. Acoust. Soc. Am.; 130(4); pp. 1888-1898; Oct. 2011.

Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).

Maxwell; Noninvasive thrombolysis using histotripsy pulsed ultrasound cavitation therapy; PhD Dissertation. University of Michigan, Ann Arbor, Michigan. Jun. 2012.

Maxwell et al.; In-vivo study of non-invasive thrombolysis by histotripsy in a porcine model; IEEE international Ultrasonics Symposium; IEEE; p. 220-223; Sep. 20, 2009.

Miller et al.; A review of in vitro bioeffects of inertial ultrasonic cavitation from a mechanistic perspective; Ultrasound in Medicine and Biology; vol. 22; pp. 1131-1154; (year of publication is sufficiently earlier than the effective U.S. filing date and any foreign priority date) 1996.

Miller et al.; Investigation of the mechanism of ARFI-based color doppler feedback of histotripsy tissue fractionation; Ultrasonic Symposium (IUS); 2013 IEEE International; 4 pages; Jul. 21-25, 2013.

Miller et al.; Real-time elastography-based monitoring of histotripsy tissue fractionation using color doppler; Ultrasonics Symposium (IUS); 2012 IEEE International; 8 pages; Oct. 7-10, 2012.

Nightingale et al.; Analysis of contrast in images generated with transient acoustic radiation force; Ultrasound Med Biol; 32(1); pp. 61-72; Jan. 2006.

Ohl et al.; Bubble dynamics, shock waves and sonoluminescence; Phil. Trans. R. Soc. Lond. A; vol. 357; pp. 269-294; (year of publication is sufficiently earlier than the effective U.S. filing date and any foreign priority date) 1999.

Okada et al.; A case of hepatocellular carcinoma treated by MR-guided focused ultrasound ablation with respiratory gating; Magn Reson Med Sci; 5(3); pp. 167-171; Oct. 2006.

Palmeri et al.; Acoustic radiation force-based elasticity imaging methods; Interface Focus; 1; pp. 553-564; Aug. 2011.

Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.

Parsons et al.; Pulsed cavitational ultrasound therapy for controlled tissue homogenization; Ultrasound in Med. & Biol.; vol. 32(1); pp. 115-129; Jan. 2006.

Pishchalnikov et al.; Cavitation Bubble Cluster Activity in the Breakage of Kidney Stones by Lithotripter Shock Waves; J Endourol.; 17(7): 435-446; Sep. 2003.

Porter et al.; Reduction in left ventricular cavitary attenuation and improvement in posterior myocardial contrast . . . ; J Am Soc Echocardiography; pp. 437-441; Jul.-Aug. 1996.

Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.

Rosenschein et al.; Ultrasound Imaging-Guided Noninvasive Ultrasound Thrombolysis: Preclinical Results; Circulation; vol. 102; pp. 238-245, Jul. 11, 2000.

Rowland et al.; MRI study of hepatic tumours following high intensity focused ultrasound surgery; British Journal of Radiology; 70; pp. 144-153; Feb. 1997.

Roy et al.; A precise technique for the measurement of acoustic cavitation thresholds and some preliminary results; Journal of the Acoustical Society of America; vol. 78(5); pp. 1799-1805; Nov. 1985.

Sapareto et al.; Thermal dose determination in cancer therapy; Int J Radiat Oncol Biol Phys; 10(6); pp. 787-800; Apr. 1984.

Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.

Sato et al.; Experimental Investigation of Phased Array Using Tapered Matching Layers. 2002 IEEE Ultrasound Symposium. vol. 2; pp. 1235-1238, Oct. 2002.

Sferruzza et al.; Generation of high power unipolar pulse with a piezocomposite transducer; In 1999 IEEE Ultrasonics Symposium Proceedings; International Symposium (Cat. No. 99CH37027); vol. 2; pp. 1125-1128; Oct. 17, 1999.

Shung; Diagnostic Ultrasound: Imaging and Blood Flow Measurements; Taylor and Francis Group, LLC; Boca Raton, FL: 207 pages; (year of pub. sufficiently earlier than effective US filing date and any foreign priority date) 2006.

Simonin et al.; Characterization of heterogeneous structure in a polymer object manufactured by stereolithography with low-frequency microechography; Journal of Materials Chemistry; vol. 6, pp. 1595-1599, Sep. 1996.

Sokolov et al.; Use of a dual-pulse lithotripter to generate a localized and intensified cavitation field; Journal of the Acoustical Society of America; vol. 110(3); pp. 1685-1695; Sep. 2001.

Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).

Souchon et al.; Visualisation of HIFU lesions using elastography of the human prostate in vivo: Preliminary results; Ultrasound Med. Biol; 29(7); pp. 1007-1015; Jul. 2003.

Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.

Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011 [retrieved on Jan. 28, 2014] from: (http://web.archive.org/web/20110720091822/http://www.histotripsy.umich.edu/index.html>.entiredocument) Jul. 2011.

Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.

(56) References Cited

OTHER PUBLICATIONS

Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.

Van Kervel et al.; A calculation scheme for the optimum design of ultrasonic transducers; Ultrasonics, vol. 21, pp. 134-140, May 1983.

Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009.

Wikipedia; Medical ultrasound; 15 pages; retrieved from the internet (https://en.wikipedia.org/w/index.php?title=Medical_utrasound&oldid=515340960) on Jan. 12, 2018.

Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).

Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.

Xu et al.; Controlled ultrasound tissue erosion: the role of dynamic interaction between insonation and microbubble activity; Journal of the Acoustical Society of America; vol. 117(1); pp. 424-435; Jan. 2005.

Xu et al.; Controlled ultrasound tissue erosion; IEEE Transaction on Ultrasonics, Ferroelectrics, and Frequency Control; vol. 51 (6); pp. 726-736; Jun. 2004.

Xu et al.; Effects of acoustic parameters on bubble cloud dynamics in ultrasound tissue erosion (histotripsy); Journal of the Acoustical Society of America; vol. 122(1); pp. 229-236; Jul. 2007.

Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.

Xu et al.; Investigation of intensity threshold for ultrasound tissue erosion; Ultrasound in Med. & Biol.; vol. 31(12); pp. 1673-1682; Dec. 2005.

Xu et al.; Optical and acoustic monitoring of bubble cloud dynamics at a tissue-fluid interface in ultrasound tissue erosion; Journal of the Acoustical Society of America; vol. 121(4): pp. 2421-2430; Apr. 2007.

Yan et al.; A review of rapid prototyping technologies and systems; Computer-Aided Design, vol. 28, pp. 307-318, Apr. 1996.

Zhang et al.; A fast tissue stiffness-dependent elastography for HIFU-induced lesions inspection; Ultrasonics; 51(8); pp. 857-869; Dec. 2011.

Zheng et al.; An acoustic backscatter-based method for localization of lesions induced by high-intensity focused ultrasound; Ultrasound Med Biol; 36(4); pp. 610-622; Apr. 2010.

Cannata et al.; U.S. Appl. No. 16/930,181 entitled "Histotripsy systems and methods," filed Jul. 15, 2020.

Xu et al.; U.S. Appl. No. 17/790,975 entitled "Systems and methods for robotically-assisted histotripsy targeeting based on mri/ct scans taken prior to treatment," filed Jul. 6, 2022.

Stopek et al.; U.S. Appl. No. 17/904,326 entitled "Minimally invasive histotripsy systems and methods," filed Aug. 16, 2022.

Maxwell et al.; U.S. Appl. No. 17/838,085 entitled "Histotripsy for thrombolysis," filed Jun. 10, 2022.

Xu et al.; U.S. Appl. No. 17/407,780 entitled "Histotripsy therapy systems and methods for the treatment of brain tissue," filed Aug. 20, 2021.

Macoskey; Acoustic methods for histotripsy feedback; (Dissertation); Biomedical Engineering and Science Computing; University of Michigan 2019; 207 pages; retrived from the internet (https://deepblue.lib.umich.edu/handle/2027.42/149988) on Feb. 2022.

Rakic et al.; U.S. Appl. No. 17/929,951 entitled "Articulating arm limiter for cavitational ultrasound therapy system," filed Sep. 6, 2022.

\* cited by examiner

HISTOTRIPSY USING VERY SHORT ULTRASOUND PULSES

CROSS REFERENCE TO RELATED APPLICATIONS

This application is a continuation of U.S. application Ser. No. 14/911,273, filed Feb. 10, 2016, which application is the national stage under 35 USC 371 of International Application No. PCT/US2014/052310, filed Aug. 22, 2014, which claims the benefit under 35 USC 119 of U.S. Provisional Application No. 61/868,992, filed Aug. 22, 2013, titled "Histotripsy Using Very Short Ultrasound Pulses", which applications are incorporated herein by reference.

STATEMENT AS TO FEDERALLY SPONSORED RESEARCH

This invention was made with Government support under Grants CA134579 and EB008998 awarded by the National Institutes of Health. The Government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure generally relates to treating tissue with bubble clouds created by ultrasound therapy.

BACKGROUND

Histotripsy, or pulsed ultrasound cavitation therapy, is a technology where extremely short, intense bursts of acoustic energy induce controlled cavitation (microbubble formation) within the focal volume. The vigorous expansion and collapse of these microbubbles mechanically homogenizes cells and tissue structures within the focal volume. This is a very different end result than the coagulative necrosis characteristic of thermal ablation. To operate within a non-thermal, Histotripsy realm; it is necessary to deliver acoustic energy in the form of high amplitude acoustic pulses with low duty cycle.

Compared with conventional focused ultrasound technologies, Histotripsy has important advantages: 1) the destructive process at the focus is mechanical, not thermal; 2) bubble clouds appear bright on ultrasound imaging thereby confirming correct targeting and localization of treatment; 3) treated tissue appears darker (hypoechoic) on ultrasound imaging, so that the operator knows what has been treated; and 4) Histotripsy produces lesions in a controlled and precise manner. It is important to emphasize that unlike microwave, radiofrequency, or high-intensity focused ultrasound (HIFU), Histotripsy is not a thermal modality.

Histotripsy produces tissue fractionation through dense energetic bubble clouds generated by short, high-pressure, ultrasound pulses. Conventional Histotripsy treatments have used longer pulses from 3 to 10 cycles wherein the lesion-producing bubble cloud generation depends on the pressure-release scattering of very high peak positive shock fronts from previously initiated, sparsely distributed bubbles (the "shock-scattering" mechanism).

In conventional Histotripsy treatments, ultrasound pulses with ≥2 acoustic cycles are applied, and the bubble cloud formation relies on the pressure release scattering of the positive shock fronts (sometimes exceeding 100 MPa, P+) from initially initiated, sparsely distributed bubbles (or a single bubble). This has been called the "shock scattering mechanism". This mechanism depends on one (or a few sparsely distributed) bubble(s) initiated with the initial negative half cycle(s) of the pulse at the focus of the transducer. A cloud of microbubbles then forms due to the pressure release backscattering of the high peak positive shock fronts from these sparsely initiated bubbles. These back-scattered high-amplitude rarefactional waves exceed the intrinsic threshold thus producing a localized dense bubble cloud. Each of the following acoustic cycles then induces further cavitation by the backscattering from the bubble cloud surface, which grows towards the transducer. As a result, an elongated dense bubble cloud growing along the acoustic axis opposite the ultrasound propagation direction is observed with the shock scattering mechanism. This shock scattering process makes the bubble cloud generation not only dependent on the peak negative pressure, but also the number of acoustic cycles and the amplitudes of the positive shocks. Without these intense shock fronts developed by nonlinear propagation, no dense bubble clouds are generated when the peak negative half-cycles are below the intrinsic threshold.

In more traditional ultrasound therapy, lesions are generated by forming an ultrasound beam into tight focal zones and using higher intensities within these foci to therapeutically modify tissue. Lesions are then generated either due to tissue heating (thermal therapy) or by mechanical agitation by energetic microbubble or bubble cloud formation (cavitation or Histotripsy). Minimum lesion size is typically determined by the diameter of the focal volume that, because of the limit due to diffraction, is around one wavelength of the propagating sound in the medium. A tightly focused ultrasound beam at 1 MHz (a typical therapeutic frequency) has a wavelength of about 1.5 mm in water or high water content tissue. Therefore, the focal diameter at 1 MHz is on the order of 1 mm or larger, depending on the transducer aperture. Using classical methods, getting smaller lesion diameters requires higher frequencies. Unfortunately, tissue penetration depth (due to increased tissue absorption and scattering) decreases with increasing frequency.

In the ultrasound cavitation based technology presented herein, much smaller diameters can be obtained at a given frequency where the lower limit in lesion size is the diameter of an individual microbubble, the primary effector in the process. Therefore, with proper pulse shaping and intensity, one can "beat" the "diffraction limit."

SUMMARY OF THE DISCLOSURE

A method of treating tissue with ultrasound energy is provided, comprising the steps of delivering an ultrasound pulse from an ultrasound therapy transducer into tissue, the ultrasound pulse having at least a portion of a peak negative pressure half-cycle that exceeds an intrinsic threshold in the tissue to produce a bubble cloud of at least one bubble in the tissue, and generating a lesion in the tissue with the bubble cloud.

In some embodiments, the ultrasound pulse comprises at least one half cycle.

In one embodiment, the intrinsic threshold is greater than or equal to 15 MPa peak negative pressure. In another embodiment, the intrinsic threshold is approximately 28 MPa peak negative pressure. In one embodiment, the intrinsic threshold is between approximately 26 MPa and 30 MPa peak negative pressure.

In some embodiments, the ultrasound pulse has a frequency between approximately 0.1 MHz and 20 MHz.

In one embodiment, the portion of the peak negative pressure half-cycle that exceeds the intrinsic threshold produces the bubble cloud while a remaining portion of the peak negative pressure half-cycle that does not exceed the intrinsic threshold does not produce the bubble cloud.

In another embodiment, the ultrasound pulse comprises a first ultrasound pulse, the method further comprising delivering a second ultrasound pulse having a smaller amplitude than the first ultrasound pulse, such that a portion of the peak negative pressure half-cycle of the second ultrasound pulse that exceeds the intrinsic threshold is smaller than the portion of the peak negative pressure half-cycle of the first ultrasound pulse that exceeds the intrinsic threshold.

In one embodiment, the second ultrasound pulse produces a smaller bubble cloud than the first ultrasound pulse.

In some embodiments, the ultrasound pulse comprises a first ultrasound pulse, the method further comprising delivering a second ultrasound pulse having a larger amplitude than the first ultrasound pulse, such that a portion of the peak negative pressure half-cycle of the second ultrasound pulse that exceeds the intrinsic threshold is larger than the portion of the peak negative pressure half-cycle of the first ultrasound pulse that exceeds the intrinsic threshold.

In one embodiment, the second ultrasound pulse produces a larger bubble cloud than the first ultrasound pulse.

In some embodiments, the bubble cloud is formed in the tissue without shock-scattering.

A method of treating tissue with ultrasound energy is provided, comprising the steps of delivering an ultrasound pulse from an ultrasound therapy transducer into tissue, the ultrasound pulse having at least a portion of a peak negative pressure half-cycle that exceeds a peak negative pressure of 28 MPa in the tissue to produce a bubble cloud in the tissue, and generating a lesion in the tissue with the cavitation nuclei.

Another method of treating tissue with ultrasound energy is provided, comprising the steps of delivering a first ultrasound pulse from an ultrasound therapy transducer into tissue, the ultrasound pulse having at least a portion of a peak negative pressure half-cycle that exceeds an intrinsic threshold in the tissue to produce a first bubble cloud in the tissue, and delivering a second ultrasound pulse having a different amplitude than the first ultrasound pulse from the ultrasound therapy transducer into tissue to produce a second bubble cloud in the tissue, such that a portion of the peak negative pressure half-cycle of the second ultrasound pulse that exceeds the intrinsic threshold is different than the portion of the peak negative pressure half-cycle of the first ultrasound pulse that exceeds the intrinsic threshold.

An ultrasound therapy system is provided, comprising an ultrasound therapy transducer, and an ultrasound therapy generator coupled to the ultrasound therapy transducer, the ultrasound therapy generator configured to drive the ultrasound therapy transducer to deliver an ultrasound pulse into tissue, the ultrasound pulse having at least a portion of a peak negative pressure half-cycle that exceeds an intrinsic threshold in the tissue to produce a bubble cloud in the tissue.

In some embodiments, the ultrasound therapy generator further comprises a controller configured to generate complex waveforms to initiate the ultrasound pulse, a high voltage power supply coupled to the controller, an amplifier configured to receive and amplify the complex waveforms from the controller and high voltage power supply, and a matching network configured to match an impedance of the ultrasound therapy transducer to the amplifier.

In some embodiments, the intrinsic threshold is greater than or equal to 15 MPa peak negative pressure. In other embodiments, the intrinsic threshold is approximately 28 MPa peak negative pressure. In another embodiment, the intrinsic threshold is between approximately 26 MPa and 30 MPa.

In some embodiments, the ultrasound pulse has a frequency between approximately 0.1 MHz and 20 MHz.

In another embodiment, the portion of the peak negative pressure half-cycle that exceeds the intrinsic threshold produces cavitation nuclei while a remaining portion of the peak negative pressure half-cycle that does not exceed the intrinsic threshold does not produce cavitation nuclei.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
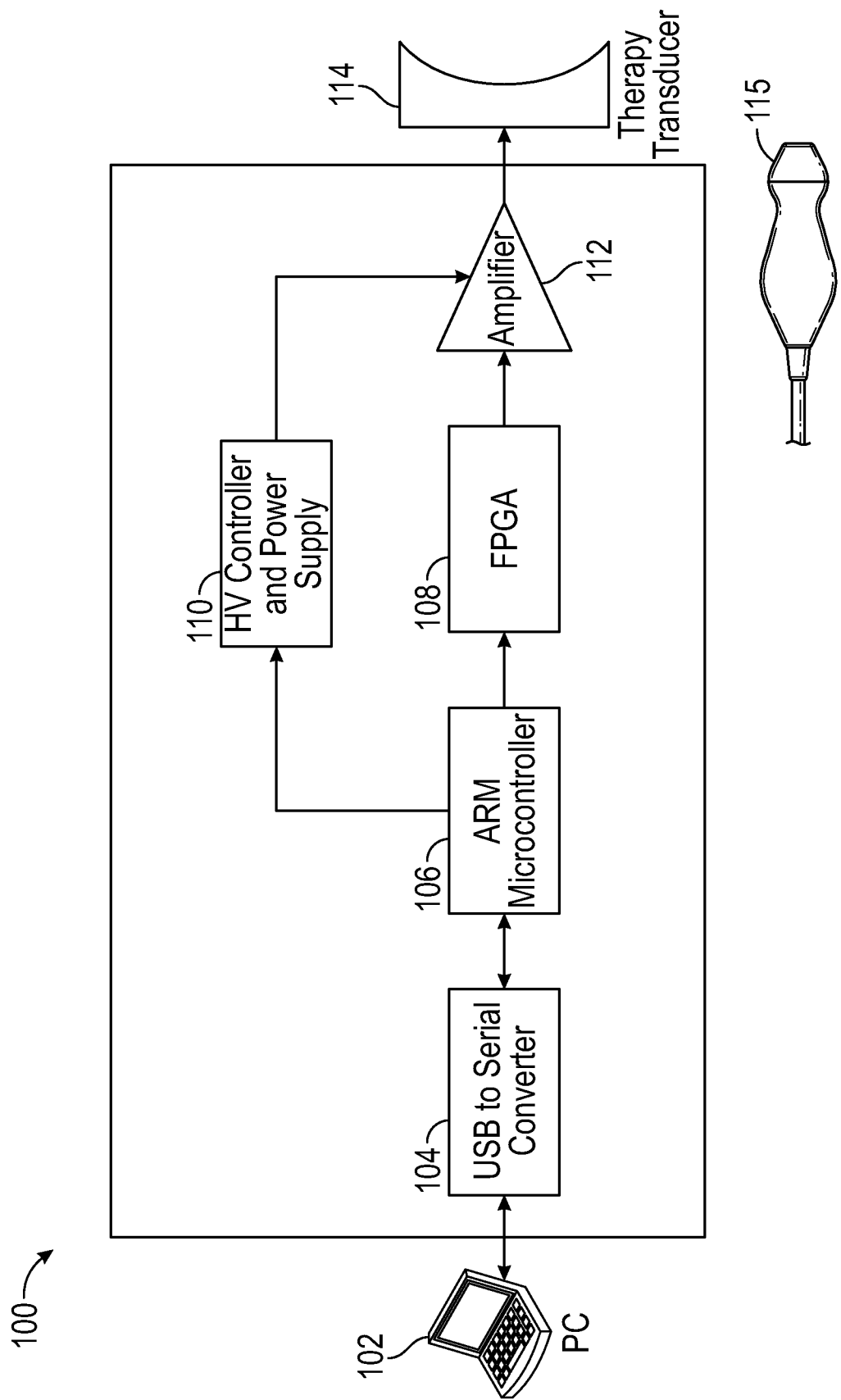
FIG. 1 shows one embodiment of a Histotripsy therapy system.

Histotripsy is a noninvasive, cavitation-based therapy that uses very short, high-pressure ultrasound pulses to generate a dense, energetic, lesion-producing bubble cloud. This Histotripsy treatment can create controlled tissue erosion when it is targeted at a fluid-tissue interface and well-demarcated tissue fractionation when it is targeted within bulk tissue. Additionally, Histotripsy has been shown to be capable of fragmenting model kidney stones using surface erosion that is mechanistically distinct from conventional shockwave lithotripsy (SWL). Histotripsy therapy can be guided and monitored using ultrasound B-mode imaging in real-time, since 1) the bubble cloud appears as a temporally changing hyperechoic region in B-mode imaging, allowing the treatment to be precisely targeted, and 2) the echogenicity of the targeted region decreases as the degree of tissue fractionation increases, which can be used as a way of monitoring lesion production (image feedback) in real-time.

In this disclosure, methods, procedures, materials, and devices that produce ultrasound cavitation lesions much smaller than the diffraction limit (the minimal size of a focal zone . . . usually around one wavelength of the incident ultrasound) are presented. The technology is based on generating an extremely consistent bubble cloud with the first peak negative half-cycle of every single or multi-cycle ultrasound pulse. This can be accomplished with an ultrasound transducer capable of generating in the target volume a peak negative pressure exceeding an intrinsic threshold (sometimes called the "homogeneous" or de novo threshold) for cavitation, i.e., the level whereby the whole volume above this peak-negative threshold generates an immediate bubble cloud throughout the supra-threshold volume. The resulting bubble cloud can generate a therapeutic lesion in the tissue. Below this threshold, individual bubbles are sparsely generated, and a bubble cloud can only be developed with a complex interaction of succeeding cycles, usually by pressure reversal scattering of high peak positive half cycles off individual sparsely distributed seed bubbles generated by previous peak negative half cycles. This process produces a somewhat chaotic multilayer cloud with unpredictable dimensions of each cloud although usually very near the focal volume.

The de novo generated bubble cloud is much more consistent in spatial distribution. Moreover, the diameter of this de novo cloud is determined by the how much of the peak negative part of the waveform exceeds the intrinsic threshold. The amplitude of the waveform can be increased to cause more of the waveform to exceed the threshold, resulting in a larger bubble cloud diameter. The resulting tissue lesion diameter from an increase in the amplitude of the waveform also increases accordingly. Thus in some embodiments, this method, and appropriate hardware, allows a lesion diameter to be modified by changing the intensity of the ultrasound pulse. Moreover, if the pulse consists of only one cycle, with only one peak negative half cycle, pulses below the threshold will not generate bubble clouds because no succeeding positive half-cycles are available for the pressure-release scattering mode to generate a complete bubble cloud. In such circumstances (below de novo threshold), the first peak negative half-cycle would only generate sparsely distributed single bubbles.

Thus, the lower limit in size of a bubble cloud generated lesion is the diameter of a single bubble which is much smaller than the wavelength of the ultrasound waveform producing that bubble, therefore, the approach described herein, which can be referred to herein as "microtripsy", is capable of generating lesion sizes much smaller than the diffraction limit determined by the frequency of the ultrasound source.

This disclosure provides mechanism for bubble cloud formation different than conventional shock-scattering bubble formation. Apparatus and methods are provided for applying ultrasound pulses into tissue or a medium in which the peak negative pressure (P−) of one or more negative half cycle(s) of the ultrasound pulses exceed(s) an intrinsic threshold of the tissue or medium, to directly form a dense bubble cloud in the tissue or medium without shock-scattering. This intrinsic threshold can be defined by a very sharp transition zone, and can be relatively insensitive to the inhomogeneities in soft tissue or the lack of dissolved gases.

Figure 2:
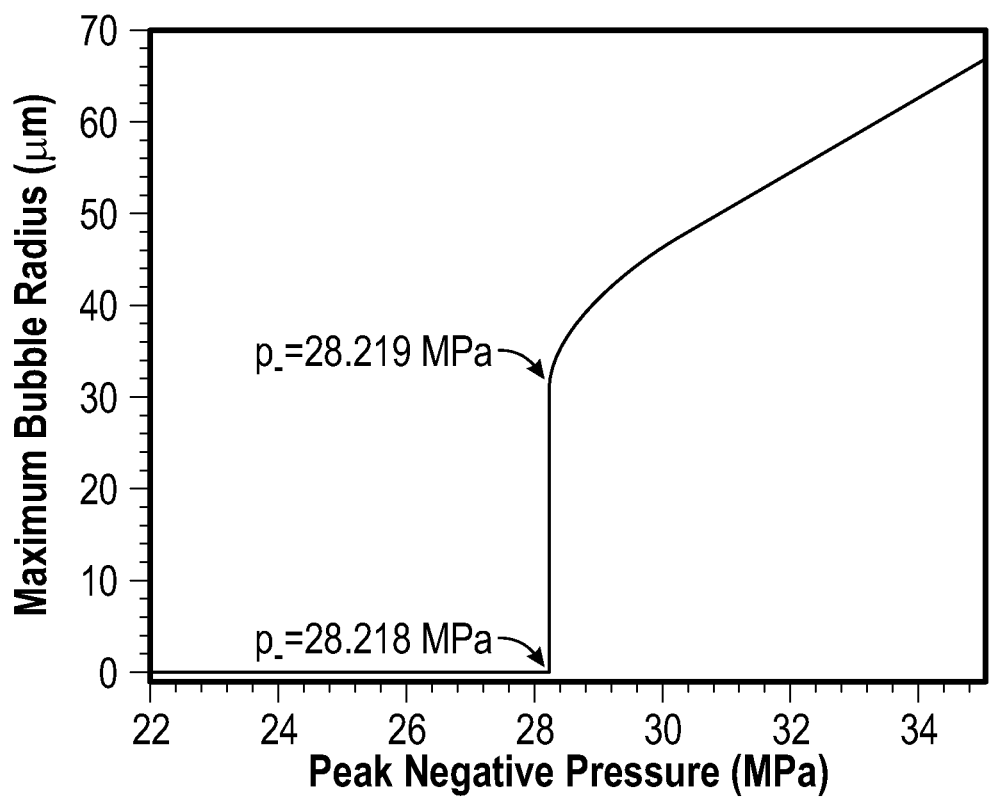
FIG. 2 illustrates an intrinsic threshold in tissue.

Moreover, this intrinsic threshold may be independent of the applied positive pressure, since the influence of shock-scattering is minimized when applying pulses less than 2 cycles. In some instances, the intrinsic threshold, where there is a high probability of cavitation (formation of a dense bubble cloud) for one single pulse is between 26.4-30.0 MPa in samples with high water content, including water, hydrogel, and soft tissue. In tissue with a higher fat content, including fatty tissues and brain tissue, the intrinsic threshold can be as low as 15 MPa. In one specific embodiment, illustrated by FIG. 2, the intrinsic threshold for a high probability of cavitation in tissue can be approximately 28 MPa. In the chart of FIG. 2, it can be seen that bubbles in this size range display a sharp threshold around a peak negative pressure of ~28 MPa. Because of the small size of the microbubbles, the cavitation threshold is nearly independent of the frequency range of interest for ultrasound therapy. For example, an intrinsic threshold with a high probability of cavitation has been identified clinically at 28.1 MPa at a frequency of 0.1 MHz, compared to a threshold of 28.4 MPa at 10 MHz.

Because of the sharp, highly repeatable threshold, at negative pressure amplitudes not significantly greater than this, a dense energetic lesion-forming cloud of microbubbles can be generated consistently with a spatial pattern similar to the part of the negative half cycles(s) exceeding the intrinsic threshold. The part of the therapy pulse exceeding intrinsic threshold, and the resulting spatial extent of the lesion forming bubble cloud, are independent of positive shocks and the somewhat chaotic shock-scattering phenomenon. Therefore, the spatial extent of the lesion generated using this mechanism is expected to be well-defined and more predictable. The lesion size can be easily controlled, even for small lesions, simply by a precise adjustment of the therapy pulse amplitude.

Apparatus and methods described herein allow high tissue penetration with minimal aberration and signal degradation while generating acceptably precise lesions. Since clinical targets shadowed by bone are highly attenuating and aberrating, some applicable targets are those reached in the brain (shadowed by skull) or thoracic cavity (shadowed by ribs), although transmission through other complex aberrating tissues is possible, e.g., for trans-uterine procedures.

Lower frequencies propagate much more cleanly through complex media, minimizing aberrations and attenuation, but produce larger lesions, based on the diffraction limit dictating larger focal zones, when conventional ultrasonic therapeutic modalities are used. By using the methods and apparatus described herein, lower frequencies can be used while, at the same time, maintaining small and precise lesion sizes.

FIG. 1 illustrates a Histotripsy system configured to generate cavitation bubbles or bubble clouds in tissue according to the methods and embodiments described herein. A Histotripsy system and generator is configured to generate complex waveforms in order to support the ultrasound pulse sequences described herein. A simplified block diagram of system 100 is shown in FIG. 1. The main components of the system are: Computer/controller 102, USB to Serial Converter 104, Microcontroller 106, FPGA (Field Programmable Gate Array) 108, High Voltage Controller and Power Supply 110, Amplifier 112, and Therapy Transducer 114.

All controls for the generator can be established using a "Histotripsy Service Tool" software that can run on the computer/controller 102 (e.g., a standard PC, laptop, tablet, or other electronic computing system) and communicates to the generator via a connector such as USB serial communication 104. Therapy, including bubble cloud cavitation and tissue ablation can be imaged and tracked in real time using an imaging system 115, such as an ultrasound imaging system or probe.

The system 100 can be configured to receive multiple sets of different driving parameters and loop them, which give the ability to the user to create wide range of custom sequences where all parameters (pulse repetition frequency (PRF), voltage amplitude, number of cycles, number of pulses per set, frequency, transducer element channels enabled, and time delays) can be set differently for every pulse generated. Time delays between pulses can be specified by the PRF for a parameter set or by specifying zero as the number of cycles per pulse.

For overall voltage amplitude regulation, level of high voltage can be changed accordingly through the Microcontroller 106 and HV Controller 110. This method cannot be used for dynamic voltage amplitude changes between two pulses since it will take too long for all capacitors on the HV line to discharge. For dynamic voltage amplitude changes between pulses, PWM (pulse width modulation) can be used at the FPGA 108 where the duty cycle of the pulse may be modulated in order to produce the desired pulse voltage and resultant pressure amplitude.

Histotripsy Service Tool

Histotripsy Service Tool is an application that can be run on any PC or computing system and may be used for controlling the system. The Histotripsy Service Tool can start/stop the therapy, set and read the level of high voltage, therapy parameters (PRF, number of cycles, duty ratio, channel enabled and delay, etc.), and set and read other service and maintenance related items.

USB to Serial Converter

USB to Serial converter 104 can convert USB combination to serial in order to communicate to the Microcontroller 106. It should be understood that other converters (or none at all) may be used in embodiments where the connection between the generator and the controller is not a USB connection.

Microcontroller

The Microcontroller 106 communicates to the computer/controller 102 (Histotripsy Service Tool) to set/read working parameters, start/stop the therapy, etc. It can use internal flash memory or other electronic storage media to store all the parameters. The Microcontroller communicates to the FPGA 108 all driving parameters that are necessary to generate complex pulsing. It also communicates using serial communication or other electronic communication to the high voltage controller and power supply 110 where it can set/read the proper level of driving voltage.

FPGA

The FPGA 108 receives the information from the Microcontroller 106 and it can generate the complex pulsing sequence that is required to drive the amplifier 112. The FPGA can run on 100 MHz clock since speed of pulsing is critical to be timed in at least 10 ns increments.

High Voltage Controller and Power Supply

The High Voltage Controller and Power Supply 110 receives the commands from the Microcontroller 106 regarding the level of DC voltage that needs to be supplied to the amplifier circuitry in order to have an adequate voltage amplitude level at the output of the amplifier.

Amplifier

The Amplifier 112 receives pulses generated by the FPGA and is supplied with high voltage from High Voltage Controller and Power Supply. It generates high voltage amplitude pulses that are fed to the Therapy Transducer 114 through the matching network components which properly matches the impedance of the therapy transducer to the impedance of the amplifier. It can be necessary to use a large number of capacitors that can store enough energy to support peak current demand during the generation of high voltage amplitude pulses.

Therapy Transducer

The Therapy Transducer 114 can be a single or multi-element ultrasound therapy transducer configured to generate and deliver the ultrasound therapy pulses described herein into tissue or other mediums. The active transducer elements of the Therapy Transducer can be piezoelectric transducer elements. In some embodiments, the transducer elements can be mounted to an acoustic lens with a common geometric focus.

Imaging System

The system can include an imaging system, such as an ultrasound imaging system, to monitor therapy and track cavitation and tissue ablation in real time. The cavitating bubble cloud generated according to the methods and system of this disclosure can appear as a temporally changing hyperechoic region in B-mode imaging, allowing the treatment to be precisely targeted.

The probability for the generation of a dense bubble cloud using a single, short pulse (≤2 cycles) is a function of the applied peak negative pressure P−. This cavitation probability curve follows a sigmoid function, given by $$P_{cav}(p_-) = \frac{1}{2}\left[1 + \mathrm{erf}\left(\frac{p_- - p_t}{\sqrt{2\sigma^2}}\right)\right], \quad (1)$$

where erf is the error function, $p_t$ is the pressure that gives a cavitation probability ($P_{cav}$) of 0.5, and σ is a variable that relates to the transition width in the cavitation probability curve, with ±σ giving the difference in pressure for cavitation probability from 0.15 to 0.85. The $p_t$'s and σ's in water, gelatin gel, and high water content soft tissue were found to be within the range of 26-30 MPa ($p_t$) and 0.8-1.4 MPa (σ).

An intrinsic pressure threshold is surprisingly similar for cavitation in water, tissue-mimicking phantoms, and tissue. The occurrence of cavitation is a stochastic process; it may or may not occur for a single pulse with finite probability, even though all parameters of the system are identical pulse to pulse. At low pressures, the probability is almost zero and with large enough pressure amplitude the probability is 1 (i.e., cavitation always happens somewhere in the focus). A key factor for microtripsy is that the intrinsic threshold is fairly sharp, meaning there is a small pressure difference between cavitation probabilities of 0 and 1. For instance, in blood or tissue, the probability is near 0 at 25 MPa peak negative pressure and nearly 1 at ~28 MPa peak negative pressure.

When a pulse passes through an ultrasound transducer focus, different positions in the medium experience different pressures. The center of the focus experiences the greatest pressure amplitude and the focal volume and dimensions are usually determined by the region which experiences peak negative pressures greater than some value relative to the maximum. In our case, we can create a map of the probability of cavitation occurring vs. position for a given pulse. Since there is a small difference in pressure between where cavitation occurs with high probability to where it occurs with very low probability, the boundary is very sharp. If the pressure output is chosen appropriately so that only the center of the focus is just above the threshold, then cavitation is likely to occur only at the focus center, a region which can be considerably smaller than 1 acoustic wavelength. In turn, it is possible that mechanical ablation of tissue smaller than 1 acoustic wavelength can be performed.

To achieve this sort of precision, short-duration (as low as ½ cycle) high peak negative pressure pulses can be generated and focused with the system described above. As described, the peak negative pressure which can be produced at the focus must exceed the intrinsic threshold to produce cavitation. Using long pulses can cause a complex interaction between a few existing microbubbles and the ultrasound pulse. This pulse will scatter from the bubbles and amplify the local pressure, causing a greater number of cavitation bubbles to expand. This limits the possible precision of microtripsy, and is necessarily circumvented by only using short pulses. Transducers to generate this sort of pressure pulse must be highly focused with high bandwidth. This output also requires an electronic driver or amplifier capable of providing the necessary high voltage to the transducer in short pulses.

As described above, an intrinsic threshold in tissue for bubble cavitation can be approximately 28 MPa. For cavitation nuclei in a size range on the order of 2.5 nm, surface tension is the dominant force controlling the threshold by the Laplace pressure. In this respect, it is similar to the Blake threshold. Systems and methods herein can include a frequency range of interest for therapy between 0.1-20 MHz. While the threshold of an individual nucleus may not be a strong function of frequency, the probability of cavitation also depends on the number of nuclei within the focal volume. As such, if an equivalent transducer with a higher frequency were applied, one would expect an incremental increase in the predicted pressure threshold due to the smaller volume of the focus. It appears that a greater negative pressure excursion will activate additional smaller nuclei coexisting with those which cavitate near the 28 MPa threshold.

Systems and methods of producing cavitation in tissue utilizing a "microtripsy" technique will now be described. An ultrasound therapy transducer, such as the transducer and Histotripsy system described in FIG. 1, can be configured to deliver one or more ultrasound pulses into tissue towards a focal point of the transducer. The one or more ultrasound pulses can include at least one negative half cycle. The system is configured to generate cavitation bubble(s) in tissue when the peak negative pressure of the waveform exceeds the intrinsic threshold in the tissue.

In some embodiments, the waveform can be generated such that only a portion of the negative half cycle has a negative pressure exceeding the intrinsic threshold. The portion of the waveform that includes a peak negative pressure greater than the intrinsic threshold in tissue will generate a bubble cloud in the tissue. Thus, the amplitude of the waveform can be adjusted to control the size of the bubble-cloud generated in the tissue. For example, the amplitude of the waveform can be reduced so that only a small portion, or the peak of the waveform exceeds the intrinsic threshold, so as to reduce the size of lesions formed in tissue from the bubble cloud. Alternatively, the amplitude of the waveform can be increased so that all or nearly all of the waveform includes a peak negative pressure that exceeds the intrinsic threshold, thereby creating a larger bubble cloud thereby increasing the size of the lesion in the tissue.

In some embodiments, the ultrasound pulse(s) can have a frequency ranging from 0.1-20 MHz or more. Reducing the frequency, such as applying ultrasound pulses to tissue at 0.1 MHz, facilitates the formation of smaller lesions in tissue with the resulting bubble cloud. Reduced frequencies an also allow bubble cloud formation deeper into tissue due to reduced attenuation.

The ultrasound pulse(s) delivered to tissue can have as few as ½ cycles, as long as at least one of the peak negative pulses exceeds the intrinsic threshold of the tissue. In one embodiment, the Histotripsy system and transducer can be configured to produce and deliver only a monopolar peak negative pulse into the tissue wherein the peak negative pulse exceeds the intrinsic threshold of the tissue.

Figure 3A:
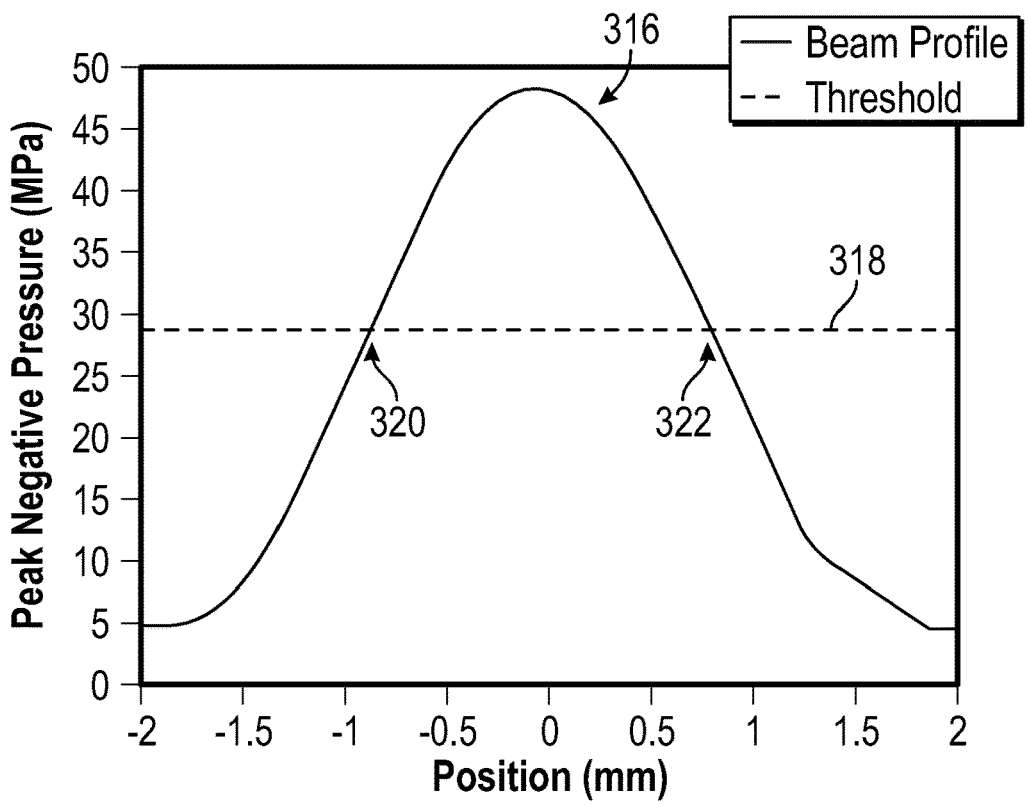
FIGS. 3A-3B show a beam profile and an intrinsic threshold in tissue.
Figure 3B:
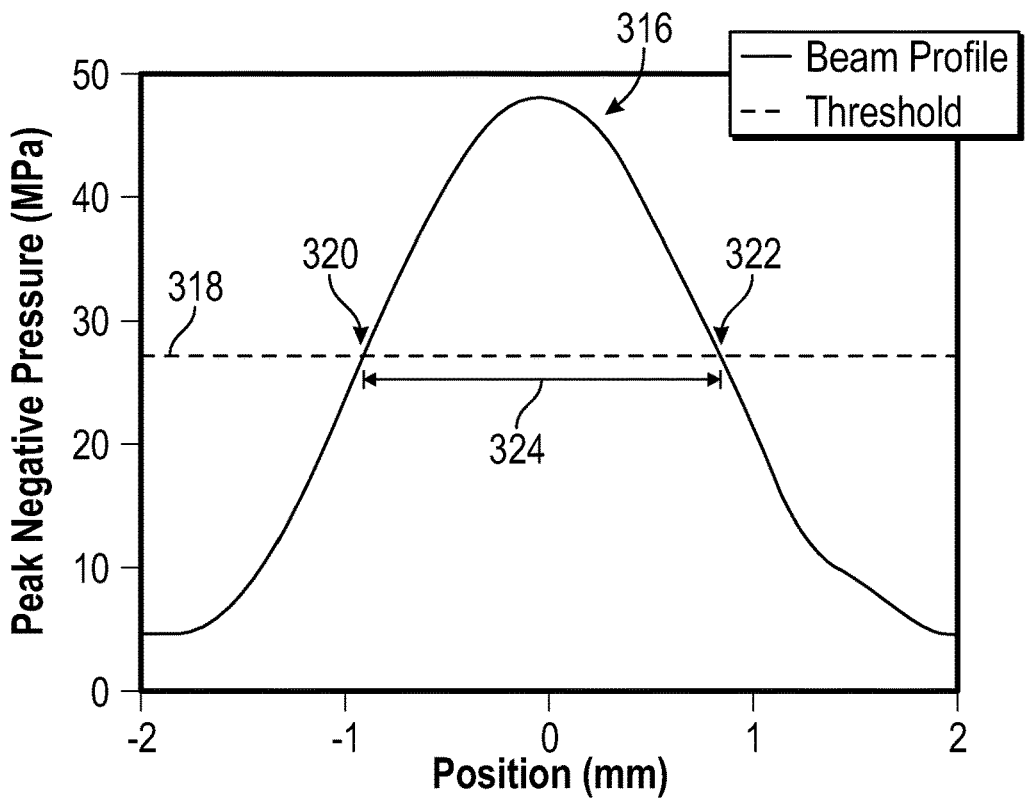

FIGS. 3A-3B illustrate a beam profile of an ultrasound pulse 316 having a negative half cycle. In the illustrated example, the pulse has a negative pressure ranging from approximately 5 MPa to a peak of approximately 50 MPa. FIG. 3A also shows the intrinsic threshold 318 at which cavitation can be formed in tissue. In this embodiment, the intrinsic threshold is approximately 28 MPa. Referring to FIG. 3A, it can be understood that the portion of the pulse that includes a peak negative pressure exceeding the intrinsic threshold 318 is configured to generate cavitation bubble(s) in the tissue with a high probability. This portion of the pulse that exceeds the intrinsic threshold is illustrated between points 320 and 322.

FIG. 3B shows how the resulting lesion size from cavitation generated by the beam profile can be estimated. In FIG. 3B, a width 324 of the lesion can be estimated by taking the distance between the two points of the beam profile that exceed the intrinsic threshold. Thus in this example, the pulse with a peak negative pressure that exceeds the intrinsic threshold between points 320 and 322 can result in a lesion size estimated to be approximately 2 mm in width.

Figure 4A:
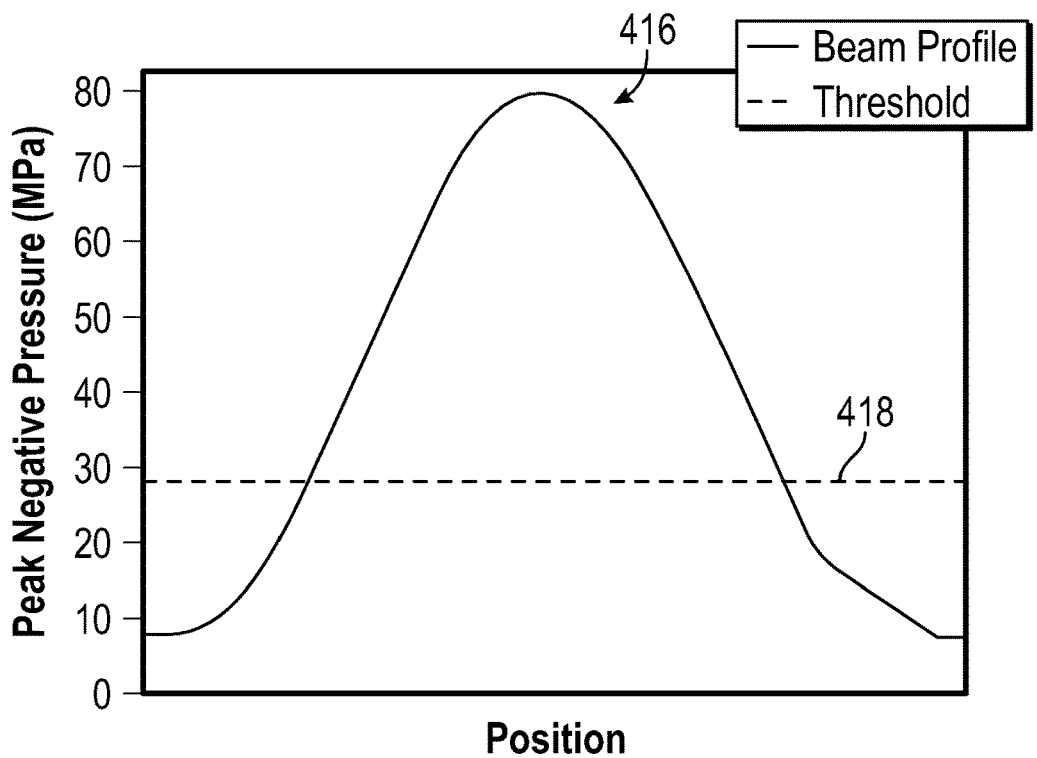
FIGS. 4A-4B show a beam profile with an adjusted amplitude and an intrinsic threshold in tissue.
Figure 4B:
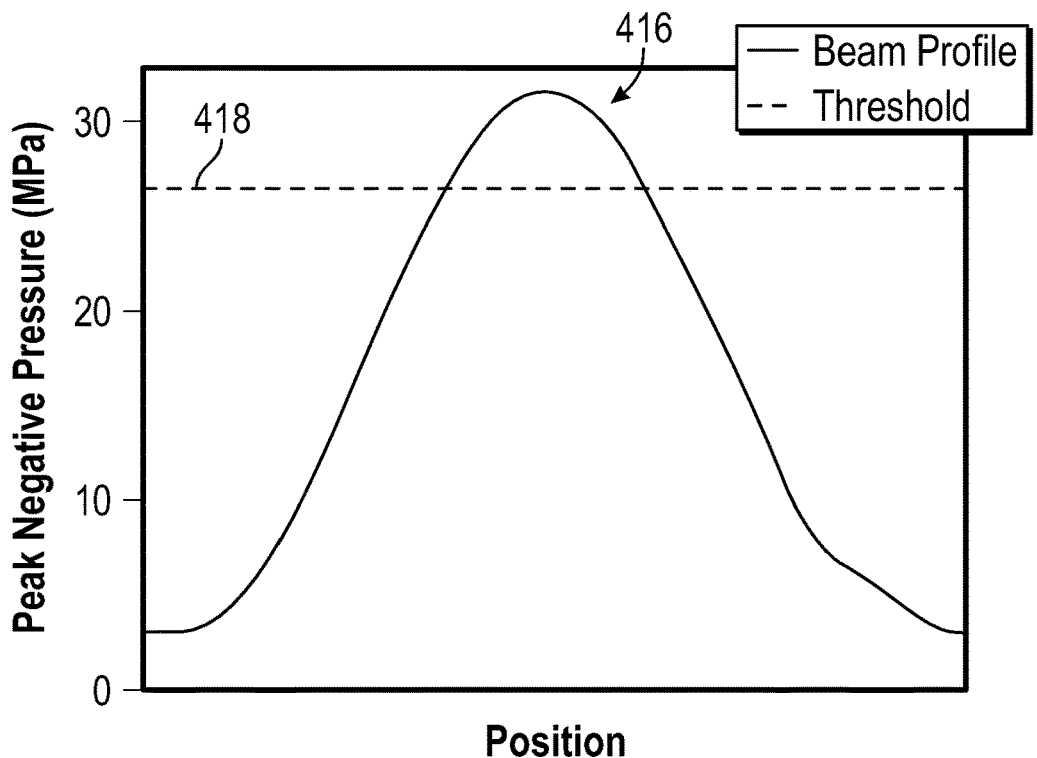

FIGS. 4A-4B illustrate how adjusting the amplitude of the ultrasound pulse can adjust the amount of cavitation produced, by changing the amount of the waveform that has a peak negative pressure exceeding the intrinsic threshold in tissue. In FIG. 4A, the ultrasound pulse 416 is shown having a negative pressure ranging from approximately 10 MPa to 80 MPa with the intrinsic threshold 418 shown at approximately 28 MPa. In this example, a large portion of the pulse 416 has a negative pressure that exceeds the intrinsic threshold. In FIG. 4B, the amplitude of a subsequent waveform has been decreased to produce a pulse having a negative pressure ranging from approximately 4 MPa to 30 MPa. In this example, only a small portion, or the very tip of the pulse, has a negative pressure that exceeds the intrinsic threshold. Reducing the amplitude of the pulse reduces the amount of the waveform that generates a bubble cloud in tissue, allowing for a smaller and more controlled bubble cloud and thus, a smaller and more controlled lesion in tissue. It should be understood that the amplitudes of subsequent waveforms can also be increased to increase the portion of the waveform that generates a bubble cloud in tissue, allowing for a larger bubble cloud and a larger lesion in tissue.

Figures 5A, 5B, 5C:
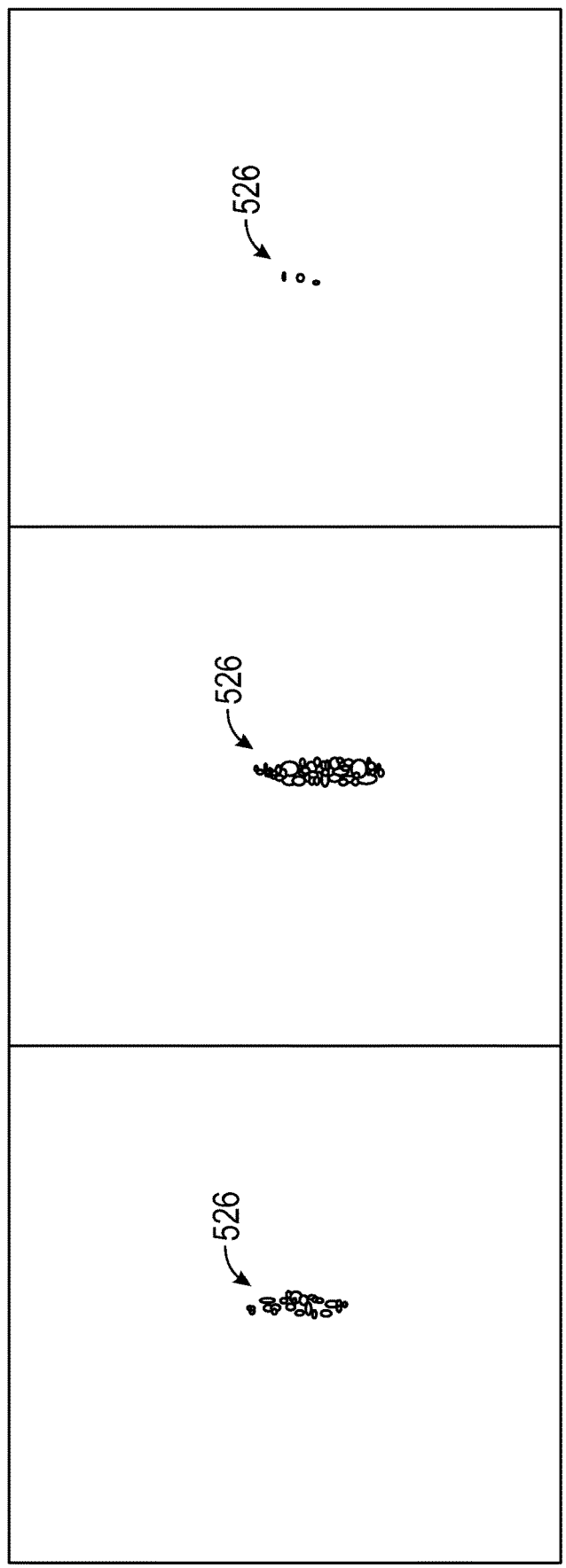
FIGS. 5A-5C illustrate the production of a bubble cloud in tissue in response to adjusting an amplitude of subsequent ultrasound pulses.

FIGS. 5A-5C illustrate how adjusting the amplitude or adjusting the portion of the negative half-cycle that exceeds the intrinsic threshold in tissue can affect the amount and size of the bubble cloud and resulting lesion in tissue. As described above, the shape of the bubble cloud generated by the intrinsic threshold mechanism is well-confined and corresponds well to the shape of the transducer focal zone. For illustrative purposes, the bubble clouds 526 shown in FIGS. 5A-5C correspond to a transducer focal zone in the shape of an ellipse or a "football" shape. FIG. 5A can illustrate a baseline bubble cloud 526. In FIG. 5B, the amount and size of the bubble cloud 526 can be increased compared to FIG. 5A by increasing an amplitude of the ultrasound pulse to cause a larger portion of the negative half-cycle to exceed the intrinsic threshold. In contrast, in FIG. 5C, the amount and size of the bubble cloud 526 can be decreased compared to FIG. 5A by decreasing an amplitude of the ultrasound pulse to cause a smaller portion of the negative half-cycle to exceed the intrinsic threshold. The resulting bubble cloud in FIG. 5C shows only a few bubbles generated in tissue.

In some embodiments, microtripsy therapy including the generation of cavitation and ablation of tissues can be monitored under real-time imaging, such as under ultrasound imaging. The real-time imaging can be used to monitor the bubble cloud formation, and also used as feedback to adjust the size of the bubble cloud. For example, in one embodiment, an initial ultrasound pulse having a peak negative pressure that exceeds the intrinsic threshold can be transmitted into tissue to generate a bubble cloud. The size of the bubble cloud can be monitored in real time with the imaging system. Next, a second ultrasound pulse with an amplitude different than the initial ultrasound pulse can be transmitted into the tissue to generate a bubble cloud. If the amplitude of the second ultrasound pulse is less than the initial ultrasound pulse but the pulse still includes a negative pressure above the intrinsic threshold, then the bubble cloud generated will be smaller than was generated with the initial pulse. If the amplitude of the second pulse is larger, then the bubble cloud generated will be greater than with the initial pulse.

Precise and controlled lesions can be generated in tissue using the intrinsic threshold mechanism of Histotripsy therapy described herein. In comparison to the bubble clouds and lesions generated by a shock-scattering mechanism, those generated by the intrinsic threshold mechanism have two advantageous characteristics. First, the shape of the bubble cloud generated by the intrinsic threshold mechanism is well-confined and corresponds well to the shape of the transducer focal zone, whereas the shape of the bubble cloud generated by the shock scattering mechanism is variable and somewhat unpredictable. Because tissue fractionation is directly correlated to the activity of the bubble cloud, the shape of the lesions produced by the intrinsic threshold mechanism is more predictable and has a better agreement to the shape of the transducer focal zone. For waveforms with a peak negative pressure near the intrinsic threshold pressure, single bubbles appear primarily in a region near the center of the focal zone. When the focal pressure is significantly in excess of the cavitation threshold, cavitation bubbles tend to occupy a region similar in shape to the focal zone for each pulse.

Second, the bubble clouds generated by the intrinsic threshold mechanism are more uniform and consistent within the region exceeding the intrinsic threshold, whereas the bubble clouds generated by the shock-scattering mechanism can be isolated to subvolumes of the focus due to complex scattering behavior. Therefore, the intrinsic threshold mechanism can potentially lead to more efficient and complete lesion development in tissue.

Moreover, using this intrinsic threshold mechanism, very small and controlled lesions can be generated by allowing only a small fraction of the focal region to exceed the cavitation threshold. For example, experiments using this method have resulted in lesions with diameters of less than 1 mm. These values were much smaller than the wavelength of the transducer ($\lambda = \sim 3$ mm for 500 kHz) used to generate the lesions. These results demonstrate that microscopic and precise lesions can be achieved using the intrinsic threshold mechanism, which can also be referred to as "microtripsy" herein.

This "microtripsy" technique based on the bubble clouds generated by the intrinsic threshold mechanism can be quite beneficial in the case where microscopic and well-defined tissue ablation is required. Especially, very precise lesions can still be achieved using a low frequency transducer by allowing only a small fraction of the focal zone to exceed the intrinsic threshold. Low frequency transducers would be favorable in applications that require long ultrasound penetration depth or where the intended targets have very attenuative overlying tissues, such as in transcranial brain therapy. Moreover, low-frequency single cycle (or close) pulses minimize phase aberration This "microtripsy" procedure uses the highly repeatable and very sharp transition zone in cavitation probability inherent to bubble cloud generation above the intrinsic threshold. Lesion sizes in both axial and lateral directions can be increased by increasing the applied peak negative pressure. These lesion sizes corresponded well to the dimensions of the focal beam profile estimated to be beyond the intrinsic cavitation threshold. This "microtripsy" technique can be significantly useful in the clinical applications where precise, microscopic tissue ablation is required, particularly where low frequencies are indicated while still maintaining small precise sub-wavelength lesions.

The aim of a "microtripsy" system can be to generate very short (e.g., as low as one half cycle) high intensity ultrasound pulses wherein the peak negative pressure of the pulse exceeds the intrinsic (or "homogeneous") threshold in the target media, such as tissue. Therefore, systems, apparatus, and methods described herein are configured to generate bubble clouds of precise and repeatable spatial distribution the diameter, which can be smaller than a wavelength of the ultrasound propagating wave inducing the bubble cloud, i.e., capable of producing lesion diameters "below" the diffraction limit.

The technology described herein allows for applications beyond the physical limitations of current thermal or cavitation based therapeutic modalities. In particular, many advantages derive from employing much lower frequencies while keeping the diameter of generated bubble clouds low (below the diffraction limit). These include: 1. Higher penetration depth, 2. Lower absorption, 3. Lower thermal complications due to heating, 4. Reduced aberration levels, especially through complex tissues including bone, and, 5. Reduced need for aberration correction methods. This can all be accomplished without suffering the usual downside (at lower frequencies) of a larger focal volume and a larger lesion.

The combination of these, and other advantages to be discussed below, will allow targets to be addresses that are currently extremely difficult by noninvasive ultrasonic means. These targets include, but are not limited to: transcranial (through the skull) noninvasive therapeutic procedures including precise lesion formation, immediate (rapid) and noninvasive treatment of stroke inducing blood clots in the brain, brain tumors, and other neural disorders treated by very precise disruption or lesion formation in neural tissues, and precise disruption of the blood brain barrier for drug delivery across drug diffusion-resistant protective membrane systems; trans-thoracic non-invasive procedures through and around the ribs. The largest application can include the treatment of liver mets, direct cardiac ablation for treatment of arrhythmias, treatment of tumors in the spleen, etc. Other applications are considered such as pediatric applications (HLHS, Trans-uterine, etc.) or thrombolysis in small vessels.

All these targets can be reached by using lower frequency ultrasound without giving up precise localization and small lesion size. Moreover, most of the treatments can be delivered by single focus inexpensive transducers without the need for the complex and expensive phased array transducers necessary for aberration correction processes. And, of course, therapy can now be delivered without the expensive means for quantifying the spatial distribution of the acoustic aberrations between the transducer and the target volume (MRI machines, invasive acoustic hydrophones or beacons and associated electronics to determine the quantitative spatial distribution of the acoustic aberrations). The methods disclosed herein are remarkably aberration resistant even not accounting for the possibility, with microtripsy, of using much lower frequencies.

With knowledge of the bubble-cloud dynamics, the pressure thresholds, and the beam pressure profiles for the transducer used for therapy, it can be possible to create a more predictive mechanical ultrasound ablative therapy with cavitation than has been previously achieved. The typical shock-scattering mechanism for forming bubble clouds, which uses multi-cycle pulses, has some limitation, in that it depends on the locations of inhomogeneties and stabilized gas bubbles in the medium to act as single bubble scatterers prior to growing the dense cloud which causes the majority of tissue disruption. Unfortunately, it is very difficult to determine the location of heterogeneous nuclei before treatment, and this can lead to clouds forming in distinct locations in the focal zone while other locations remain completely uncavitated. In contrast, the single pressure excursion pulse described herein can generate cavitation uniformly within the focal zone. While cavitation has generally been regarded as unpredictable in ultrasound therapy, the pulsing regime of this disclosure can create a very controllable situation for planning therapy. Around the cavitation threshold, single bubbles can be generated by a single pulse. In contrast to thermal ultrasound therapy, where applying too great of an acoustic dose can cause damage to collateral tissue by diffusion of heat, the damage with histotripsy can be limited to the focal region and overtreating may have few negative consequences, as the spatial boundary between very high probability and low probability is very narrow because of the intrinsically small value for the probability transition zone σ.

The advantages of bubble cloud generation with as little as a half cycle (or just a few cycles) high intensity pulses with peak negative pressures exceeding the de novo (or homogeneous) threshold are as follows:

The bubble cloud extent can be controlled by the fraction of the peak negative waveform exceeding the intrinsic threshold, which is proportional to pulse intensity. Therefore, the minimum lesion size is limited only by the size of the smallest bubble cloud possible which is the diameter of a single bubble. Bubbles formed near the threshold for a 1 MHz transducer are 100-200 μm diameter in tissue, which is 0.06-0.13 wavelengths. Bubbles will grow inversely proportionate to frequency, but their fraction of a wavelength will be similar for most cases. Tissue confinement can limit the maximum expansion of bubbles below these values as well. Therefore, instead of the diffraction limit of several millimeters, the minimum lesion diameter may be as small as 100 micrometers, or a reduction in lesion diameter of an order of magnitude below the diffraction limit.

Smaller bubble clouds mean, for a given fixed lesion diameter, much lower frequencies can be used increasing depth of penetration and decreasing absorption and scattering.

Lower absorption means greatly reduced heating and unwanted hot spots, particularly at tissue boundaries. Such undesired (and unpredictable) thermal consequences often define the limits for certain ultrasound therapies at depth.

Tissue aberrations decrease with frequency allowing much cleaner beams to be formed through complex tissues reducing the need for aberration correction.

The "microtripsy" approach uses the portion of the ultrasound waveform above the intrinsic threshold to generate bubble clouds, thus allowing a large degree of protection against adverse effects of high ultrasound beam side-lobes.

Lower aberrations levels (from the allowed lower frequencies) and the relative insensitivity to aberrations will allow greatly reduced overall system expense by greatly reducing the need for expensive aberration correction hardware and software.

Lower frequencies and lack of need for aberration correction schemes will allow clinical targets like the brain and liver to be treated through the skull and ribs, respectively, without an increase in lesion size.

The de novo generated bubble clouds are remarkably consistent in size for single cycle pulses, and the size can be adjusted by adjusting the pulse amplitude without a need to change the source frequency or the source aperture. As stated several times before, this bubble cloud diameter, and resulting lesion diameter, can be much below the diffraction limit in size.

When bubble clouds are generated by de novo single pulse Histotripsy, the treated volume is remarkably consistent from pulse to pulse with the bubbles forming at random (not predetermined) locations in the focal volume. In other approaches to generating bubble clouds, the location of individual bubbles can depend on memory effects from previous pulses (due to persistent bubble remnants or micronuclei). This memory effect often results in clouds being generated non-homogeneously in the focal volume with some sub-volumes generating no bubbles at all. This results in non-homogeneous lesions in the focal volume with islands of untreated tissues. Many additional pulses are necessary to expand these treated zones to include the un-homogenized islands. Although there are active and passive ways to avoid this memory effect, they require greater complexity.

The zone raised above the de novo threshold (the "de novo volume") generates bubbles throughout this volume regardless of pre-existing nuclei due to the memory effect, or due to natural dissolved gas, or other cavitation nuclei, in the target volume. Because the de novo threshold is higher than for other forms of cavitation, bubble clouds in the de novo volume tend to be remarkably consistent from pulse to pulse and in different environments.

Because the optimum "microtripsy" pulse comprises at least a single half cycle, the thermal potential of this therapy is minimized due to the very short pulses.

Because the de novo volume is resistant to memory and other pre-existing bubble clouds, much greater pulse repetition frequencies (PRFs) are possible before remnants of previous bubble clouds interfere in a destructive manner in the generation of the latest bubble cloud, a phenomenon common at higher PRFs in other Histotripsy approaches.

Short single cycle pulses are more resistant to aberrations because less time is available for multi-path scattered signals to form up constructively to produce higher side-lobes.

Since the bubble clouds in the de novo volume are not dependent on pressure release scattering from previous bubbles randomly generated by separate multi-cycle bursts or succeeding cycles in a given burst, all below the de novo threshold, the need for more than one initiation pulse (or burst) to get a fully formed bubble cloud disappears.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium.

Furthermore, the methods and processes described above can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating tissue with ultrasound energy, comprising the steps of:
   delivering a first ultrasound waveform from an ultrasound therapy transducer into tissue, the first ultrasound waveform having a first amplitude such that only a first portion of a peak negative half-cycle of the ultrasound waveform exceeds an intrinsic threshold in the tissue to produce a first bubble cloud having a first diameter in the tissue;
   generating a first lesion in the tissue with the first bubble cloud;
   subsequently delivering a second ultrasound waveform from the ultrasound therapy transducer into tissue, the second ultrasound waveform having a second amplitude different than the first amplitude such that only a second portion of the peak negative half-cycle of the second ultrasound waveform exceeds the intrinsic threshold in the tissue to produce a second bubble cloud having a second diameter in the tissue, wherein the second portion of the peak negative half-cycle of the second ultrasound waveform that exceeds the intrinsic threshold is greater than the first portion of the peak negative half-cycle of the first ultrasound waveform that exceeds the intrinsic threshold; and
   generating a second lesion in the tissue with the second bubble cloud.

2. The method of claim 1, wherein the first ultrasound waveform consists of only a monopolar peak negative pulse having a peak negative pressure that exceeds the intrinsic threshold in the tissue.

3. The method of claim 1, wherein the first ultrasound waveform comprises one half cycle.

4. The method of claim 1 wherein the intrinsic threshold is greater than or equal to 15 MPa peak negative pressure.

5. The method of claim 1 wherein the intrinsic threshold is 28 MPa peak negative pressure.

6. The method of claim 1 wherein the intrinsic threshold is between 26 MPa and 30 MPa peak negative pressure.

7. The method of claim 1 wherein the first ultrasound waveform has a frequency between 0.1 MHz and 20 MHz.

8. The method of claim 1, wherein the first bubble cloud is formed in the tissue without shock-scattering.

9. The method of claim 1, wherein a diameter of the first lesion is smaller than a wavelength of the first ultrasound waveform.

10. The method of claim 1, wherein a shape of the first bubble cloud corresponds to a shape of a focal zone of the ultrasound therapy transducer.

11. The method of claim 1, wherein the first lesion has a diameter less than 1 mm.

12. The method of claim 1, wherein the second amplitude is greater than the first amplitude.

13. A method of treating tissue with ultrasound energy, comprising the steps of:
   delivering a first ultrasound waveform consisting of only a first monopolar peak negative pulse from an ultrasound therapy transducer into tissue, the first ultrasound waveform having a first amplitude and a first peak negative pressure that exceeds an intrinsic threshold in the tissue to produce a first bubble cloud having a first diameter in the tissue;
   generating a first lesion in the tissue with the first bubble cloud;
   subsequently delivering a second ultrasound waveform consisting of only a second monopolar peak negative pulse from the ultrasound therapy transducer into tissue, the second ultrasound waveform having a second amplitude different than the first amplitude and a second peak negative pressure that exceeds the intrinsic threshold in the tissue to produce a second bubble cloud having a second diameter in the tissue; and
   generating a second lesion in the tissue with the second bubble cloud.

14. A method of treating tissue with ultrasound energy, comprising the steps of:
   delivering a first ultrasound waveform from an ultrasound therapy transducer into tissue, the first ultrasound waveform having a first amplitude such that only a first portion of a peak negative half-cycle of the ultrasound waveform exceeds an intrinsic threshold in the tissue to produce a first bubble cloud having a first diameter in the tissue;
   generating a first lesion in the tissue with the first bubble cloud;
   subsequently delivering a second ultrasound waveform from the ultrasound therapy transducer into tissue, the second ultrasound waveform having a second amplitude different than the first amplitude such that only a second portion of the peak negative half-cycle of the second ultrasound waveform exceeds the intrinsic threshold in the tissue to produce a second bubble cloud having a second diameter in the tissue, wherein the second portion of the peak negative half-cycle of the second ultrasound waveform that exceeds the intrinsic threshold is less than the first portion of the peak negative half-cycle of the first ultrasound waveform that exceeds the intrinsic threshold; and generating a second lesion in the tissue with the second bubble cloud.

15. The method of claim 14, wherein the first ultrasound waveform comprises one half cycle.

16. The method of claim 14, wherein the intrinsic threshold is greater than or equal to 15 MPa peak negative pressure.

17. The method of claim 14, wherein the intrinsic threshold is 28 MPa peak negative pressure.

18. The method of claim 14, wherein the intrinsic threshold is between 26 MPa and 30 MPa peak negative pressure.

19. The method of claim 14, wherein the first ultrasound waveform has a frequency between 0.1 MHz and 20 MHz.

20. The method of claim 14, wherein the first bubble cloud is formed in the tissue without shock-scattering.

21. The method of claim 14, wherein a diameter of the first lesion is smaller than a wavelength of the first ultrasound waveform.

22. The method of claim 14, wherein a shape of the first bubble cloud corresponds to a shape of a focal zone of the ultrasound therapy transducer.

23. The method of claim 14, wherein the first lesion has a diameter less than 1 mm.

24. The method of claim 14, wherein the second amplitude is less than the first amplitude.

25. A method of treating tissue with ultrasound energy, comprising the steps of:

delivering a first ultrasound waveform consisting of only a first monopolar peak negative pulse from an ultrasound therapy transducer into tissue, the first ultrasound waveform having a first amplitude such that only a first portion of a peak negative half-cycle of the ultrasound waveform exceeds an intrinsic threshold in the tissue to produce a first bubble cloud having a first diameter in the tissue;

generating a first lesion in the tissue with the first bubble cloud;

subsequently delivering a second ultrasound waveform from the ultrasound therapy transducer into tissue, the second ultrasound waveform having a second amplitude different than the first amplitude such that only a second portion of the peak negative half-cycle of the second ultrasound waveform exceeds the intrinsic threshold in the tissue to produce a second bubble cloud having a second diameter in the tissue; and generating a second lesion in the tissue with the second bubble cloud.

* * * * *